United States Patent
Engelhardt

(10) Patent No.: US 9,428,513 B2
(45) Date of Patent: Aug. 30, 2016

(54) TRIAZOLOPYRAZINE

(71) Applicant: Boehringer Ingelheim International GmbH, Ingelheim am Rhein (DE)

(72) Inventor: Harald Engelhardt, Ebreichsdorf (AU)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/532,405

(22) Filed: Nov. 4, 2014

(65) Prior Publication Data

US 2015/0133447 A1     May 14, 2015

(30) Foreign Application Priority Data

Nov. 7, 2013   (EP) .................................... 13192002

(51) Int. Cl.
*C07D 487/04*   (2006.01)
*C07D 519/00*   (2006.01)

(52) U.S. Cl.
CPC ............ *C07D 487/04* (2013.01); *C07D 519/00* (2013.01)

(58) Field of Classification Search
CPC .................................................... C07D 487/04
See application file for complete search history.

(56) References Cited

U.S. PATENT DOCUMENTS

2014/0142098 A1   5/2014   Engelhardt et al.

FOREIGN PATENT DOCUMENTS

| | | |
|---|---|---|
| EP | 1050535 A1 | 11/2000 |
| WO | 2012174487 A2 | 12/2012 |
| WO | 2014076237 A1 | 5/2014 |

OTHER PUBLICATIONS

International Search Report and Written Opinion for corresponding application PCT/EP2014/074069, date of mailing Jan. 5, 2015.

*Primary Examiner* — Rebecca Anderson
(74) *Attorney, Agent, or Firm* — Michael P. Morris; Usha R. Patel

(57) ABSTRACT

The present invention encompasses compounds of general formula (I)

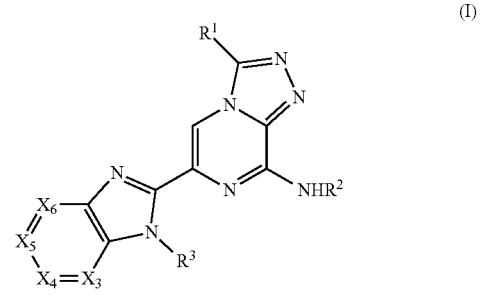

wherein the groups $R^1$ to $R^3$, $X_3$ to $X_6$ have the meanings given in the claims and in the specification. The compounds of the invention are suitable for the treatment of diseases characterized by excessive or abnormal cell proliferation pharmaceutical preparations containing such compounds and their uses as a medicament.

16 Claims, No Drawings

TRIAZOLOPYRAZINE

This invention relates to compounds of the general formula (I)

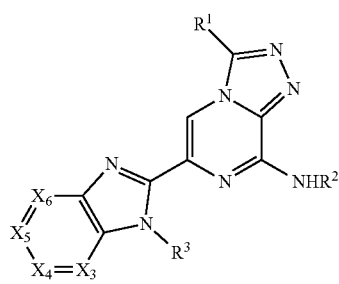
(I)

wherein the groups $R^1$ to $R^3$, $X_3$ to $X_6$ have the meanings given below. The compounds of the invention are suitable for the treatment of diseases characterized by excessive or abnormal cell proliferation, pharmaceutical preparations containing such compounds and their uses as a medicament. The compounds of the invention are BRD4 inhibitors.

BACKGROUND OF THE INVENTION

Histone acetylation is most usually associated with the activation of gene transcription, as the modification loosens the interaction of the DNA and the histone octomer by changing the electrostatics. In addition to this physical change, specific proteins bind to acetylated lysine residues within histones to read the epigenetic code. Bromodomains are small (about 110 amino acid) distinct domains within proteins that bind to acetylated lysine resides commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRD-T) which contain tandem bromodomains capable of binding to two acetylated lysine residues in close proximity, increasing the specificity of the interaction. Recent research has established a compelling rationale for targeting BRD4 in cancer. BRD4 remains bound to transcriptional start sites of genes expressed during the entry into the G1 phase of the cell cycle, and is functioning to recruit the positive transcription elongation factor complex (P-TEFb), resulting in increased expression of growth promoting genes (Yang and Zhou, Mol. Cell. Biol. 28, 967, 2008). Importantly, BRD4 has been identified as a component of a recurrent t(15; 19) chromosomal translocation in an aggressive form of human squamous carcinoma (French et al., Cancer Res. 63, 304, 2003). Such translocations express the tandem N-terminal bromodomains of BRD4 as an in-frame chimera with the NUT (nuclear protein in testis) protein, genetically defining the so-called NUT midline carcinoma (NMC). Functional studies in patient-derived NMC cell lines have validated the essential role of the BRD4-NUT oncoprotein in maintaining the proliferation and the differentiation block of these malignant cells. In addition, BRD4 has been identified as a critical sensitivity determinant in a genetically defined AML mouse model (Zuber et al., Nature 2011 478(7370):524-8). Suppression of BRD4 led to robust anti-leukemic effects in vitro and in vivo, accompanied by terminal myeloid differentiation. Interestingly, BRD4 inhibition triggered MYC downregulation in a broad array of mouse and human leukemia cell lines examined, indicating that small molecule BRD4 inhibitors may provide a means to suppress the MYC pathway in a range of AML subtypes.

Finally, the other family members of the BET family have also been reported to have some function in controlling or executing aspects of the cell cycle, and have been shown to remain in complex with chromosomes during cell division—suggesting a role in the maintenance of epigenetic memory (Leroy et al, Mol. Cell. 2008 30(1):51-60).

Examples of bromodomain inhibitors are benzodiazepine derivatives, disclosed in WO2011/054553, and imidazo[4,5] quinoline derivatives, disclosed in WO2011/054846.

Thus, there is the need to provide BRD4 inhibitors useful for the prevention and/or treatment of diseases characterized by excessive or abnormal cell proliferation, such as cancer.

DETAILED DESCRIPTION OF THE INVENTION

The present invention relates to compounds of formula (I)

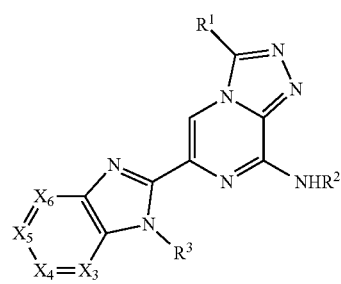
(I)

wherein,
$R^1$ is —$C_{1-3}$alkyl or —$C_{1-3}$ haloalkyl;
$R^2$ is selected from hydrogen or —$C_{1-3}$alkyl, or
$R^2$ is selected from 4-7 membered heterocycloalkyl, wherein the heterocycloalkyl group can be optionally and independently substituted with one or more groups independently selected from —$C_{1-3}$alkyl, —C(O)($C_{1-3}$alkyl)$_2$, —S(O)$_2$($C_{1-3}$ alkyl)$_2$;
$R^3$ is —$C_{1-4}$alkyl substituted with one or more groups independently selected from halogen, —$C_{1-2}$haloalkyl, —O—$C_{1-3}$ alkyl, —O—$C_{1-3}$ halolkyl, 4-7 membered heterocycloalkyl, —$C_{3-7}$ cycloalkyl;
$X_3$ is —CH= or —N=;
$X_4$ is —CR$^4$= or —N=;
$X_5$ is —CR$^5$= or —N=;
$X_6$ is —CH= or —N=;
wherein none, one or two $X_3$ to $X_6$ can be —N=;
$R^4$ is selected from hydrogen, halogen, —CN, —NH$_2$, —O—$C_{1-3}$alkyl, —N($C_{1-3}$alkyl)$_2$, —C(O)N($C_{1-3}$ alkyl)$_2$ and —$C_{1-5}$alkyl, wherein the —$C_{1-5}$alkyl group can be optionally and independently substituted with one or more groups independently selected from halogen or —CN, or
$R^4$ is selected from 4-7 membered heterocycloalkyl, wherein the heterocycloalkyl group can be optionally and independently substituted with one or more groups independently selected from —$C_{1-3}$alkyl, or
$R^4$ is a —$C_{3-6}$cycloalkyl wherein the cycloalkyl group can be optionally and independently substituted with one or more groups independently selected from $C_{1-3}$alkyl, —$C_{1-3}$haloalkyl and halogen;

$R^5$ is selected from hydrogen, halogen, —N(C$_{1-3}$alkyl)$_2$, or $R^5$ is selected from 4-7 membered heterocycloalkyl, wherein the heterocycloalkyl group can be optionally and independently substituted with one or more groups independently selected from —C$_{1-3}$alkyl;

wherein $R^4$ and $R^5$ cannot be both hydrogen;

or when X$_4$ is —CR$^4$ and X$_5$ is —CR$^5$, $R^4$ and $R^5$ together can form 5 membered heterocycloalkyl of the following types:

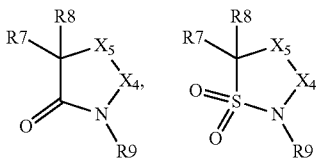

$R^7$ is selected from —C$_{1-3}$alkyl, and —C$_{1-3}$haloalkyl;
$R^8$ is selected from —C$_{1-3}$ alkyl, and —C$_{1-3}$haloalkyl;
$R^9$ is selected from —C$_{1-3}$alkyl, and —C$_{1-3}$haloalkyl;
and wherein the compounds of formula (I) may be optionally be present in the form of salts.

In a preferred embodiment, the present invention relates to compounds of formula (Ia)

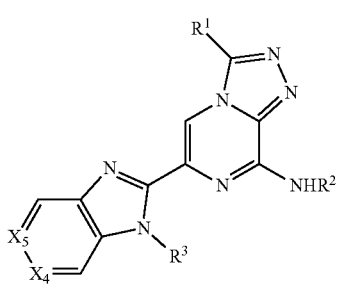

(Ia)

wherein,
$R^1$ is —C$_{1-3}$alkyl or —C$_{1-3}$ haloalkyl;
$R^2$ is selected from —C$_{1-3}$ alkyl;
$R^3$ is —C$_{1-4}$alkyl substituted with one or more groups independently selected from halogen, —C$_{1-2}$haloalkyl, —O—C$_{1-3}$ alkyl, —O—C$_{1-3}$ halolkyl, 4-7 membered heterocycloalkyl, —C$_{3-7}$ cycloalkyl;
X$_4$ is —CR$^4$═ or —N═;
X$_5$ is —CR$^5$═ or —N═;
$R^4$ is selected from halogen, —CN, —NH$_2$, —O—C$_{1-3}$alkyl, —N(C$_{1-3}$alkyl)$_2$, —C(O)N(C$_{1-3}$alkyl)$_2$ and —C$_{1-5}$alkyl, wherein the —C$_{1-5}$alkyl group can be optionally and independently substituted with one or more groups independently selected from halogen or —CN, or
$R^4$ is selected 4-7 membered heterocycloalkyl, wherein the heterocycloalkyl group can be optionally and independently substituted with one or more groups independently selected from —C$_{1-3}$alkyl, or
$R^4$ is a —C$_{3-6}$cycloalkyl wherein the cycloalkyl group can be optionally and independently substituted with one or more groups independently selected from C$_{1-3}$alkyl, —C$_{1-3}$haloalkyl and halogen;
$R^5$ is selected from —H or,
when X$_4$ is —CR$^4$ and X$_5$ is —CR$^5$, $R^4$ and $R^5$ together can form 5 membered heterocycloalkyl of the following type:

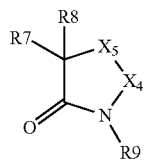

$R^7$ is selected from —C$_{1-3}$alkyl, and —C$_{1-3}$haloalkyl;
$R^8$ is selected from —C$_{1-3}$ alkyl, and —C$_{1-3}$haloalkyl;
$R^9$ is selected from —C$_{1-3}$alkyl, and —C$_{1-3}$haloalkyl;
and wherein the compounds of formula (Ia) may be optionally be present in the form of salts.

In a preferred embodiment, the invention relates to compounds of formula (I), wherein X$_3$ is —CH═.

In a preferred embodiment, the invention relates to compounds of formula (I), wherein X$_6$ is —CH═.

In a preferred embodiment, the invention relates to compounds of formula (I) or (Ia), wherein $R^1$ is —CH$_3$.

In a preferred embodiment, the invention relates to compounds of formula (I) or (Ia), wherein $R^2$ is selected from hydrogen, —C$_{1-3}$alkyl and 6 membered heterocyclyl substituted with —C$_{1-3}$ alkyl or —S(O)$_2$(C$_{1-3}$ alkyl)$_2$.

In a preferred embodiment, the invention relates to compounds of formula (I) or (Ia), wherein $R^2$ is hydrogen, isopropyl, methyl or piperidine, wherein the piperidine is N-substituted with methyl or —SO$_2$CH$_3$.

In a preferred embodiment, the invention relates to compounds of formula (I) or (Ia), wherein $R^2$ is isopropyl or methyl.

In a preferred embodiment, the invention relates to compounds of formula (Ia), wherein $R^2$ is isopropyl or methyl.

In a preferred embodiment, the invention relates to compounds of formula (I) or (Ia), wherein $R^3$ is selected from —C$_{1-4}$alkyl substituted with one group selected from —O—C$_{1-3}$alkyl, —C$_{1-2}$haloalkyl, —C$_{3-7}$ cycloalkyl and 5 membered heterocycloalkyl.

In a preferred embodiment, the invention relates to compounds of formula (Ia), wherein $R^3$ is selected from —C$_{1-4}$alkyl substituted with one group selected from —O—C$_{1-3}$ alkyl and 5 membered heterocycloalkyl.

In a preferred embodiment, the invention relates to compounds of formula (I) or (Ia), wherein $R^3$ is selected from —(CH$_2$)$_2$—O—CH$_3$, —CH(CH$_3$)—CH$_2$—O—CH$_3$, —(CH$_2$)$_2$—O—CH(CH$_3$)$_2$, —(CH$_2$)$_2$—O—CH$_2$—CH$_3$, —CH$_2$-tetrahydrofuran, —CH(CH$_3$)—CH$_2$-cyclopropyl and —CH(CH$_3$)—CH$_2$—CF$_3$.

In a preferred embodiment, the invention relates to compounds of formula (Ia), wherein $R^3$ is —(CH$_2$)$_2$—O—CH$_3$, —CH(CH$_3$)—CH$_2$—O—CH$_3$, —(CH$_2$)$_2$—O—CH(CH$_3$)$_2$, —(CH$_2$)$_2$—O—CH$_2$—CH$_3$, —CH$_2$-tetrahydrofuran.

In a preferred embodiment, the invention relates to compounds of formula (I) or (Ia), wherein $R^4$ is selected from hydrogen, —C$_{1-3}$alkyl, NH$_2$, and 6 membered heterocycloalkyl, which heterocycloalkyl might be optionally substituted by one methyl.

In a preferred embodiment, the invention relates to compounds of formula (I) or (Ia), wherein $R^4$ is selected from hydrogen, —CH(CH$_3$)$_2$, NH$_2$, tetrahydropyran and morpholine, which morpholine is optionally substituted with one methyl.

In a preferred embodiment, the invention relates to compounds of formula (Ia), wherein $R^4$ is selected from —C$_{1-3}$alkyl or 6 membered heterocycloalkyl, which heterocycloalkyl might be optionally substituted by one methyl.

In a preferred embodiment, the invention relates to compounds of formula (Ia), wherein $R^4$ is selected from —CH($CH_3$)$_2$, tetrahydropyran and morpholine, which morpholine is optionally substituted with methyl.

In a preferred embodiment, the invention relates to compounds of formula (I) or (Ia), wherein $R^5$ is hydrogen or morpholine.

In any embodiment $R^4$ and $R^5$ cannot be both hydrogen.

In a preferred embodiment, the invention relates to compounds of formula (I) or (Ia), wherein $X_4$ is —$CR^4$ and $X_5$ is —$CR^5$, $R^4$ and $R^5$ are taken together to form

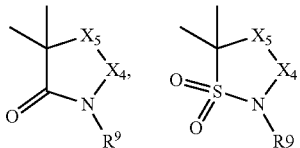

wherein $R^9$ is selected from —$C_{1-3}$alkyl.

In a preferred embodiment, the invention relates to compounds of formula (Ia), wherein when $X_4$ is —$CR^4$ and $X_5$ is —$CR^5$, $R^4$ and $R^5$ are taken together to form

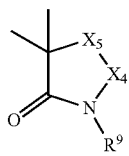

and wherein $R^9$ is selected from —$C_{1-3}$alkyl.

In a preferred embodiment, the invention relates to compounds of formula (I) or (Ia), wherein $X_4$ is —$CR^4$ and $X_5$ is —$CR^5$, $R^4$ and $R^5$ are taken together to form

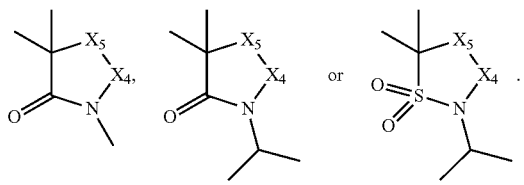

In a preferred embodiment, the invention relates to compounds of formula (Ia), wherein when $X_4$ is —$CR^4$ and $X_5$ is —$CR^5$, $R^4$ and $R^5$ are taken together to form

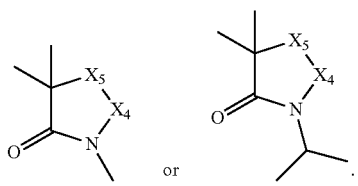

In a preferred embodiment, the invention relates to compounds of formula (Ia), wherein $R^9$ is methyl, ethyl or isopropyl.

In a preferred embodiment, the invention relates to compounds of formula (Ia), wherein $R^9$ is methyl or isopropyl In a preferred embodiment, the invention relates to compounds of formula (Ia), wherein $X_5$ is nitrogen.

In a preferred embodiment, the invention relates to compounds of formula (Ia), wherein $X_5$ is —CH—.

In a preferred embodiment, the invention relates to compounds of formula (Ia), wherein $R^5$ is hydrogen.

In a further embodiment, the invention relates to compounds of formula (I) or (Ia) for use in the treatment of cancer.

In a further embodiment, the invention relates to compound of general formula (I) or (Ia) according to anyone of the embodiments described herein in the description and the claims—or the pharmaceutically acceptable salts thereof—for use in the treatment and/or prevention of cancer.

In a further embodiment, the invention relates to pharmaceutical preparation comprising as active substance one or more compounds of general formula (I) or (Ia) according to anyone of the embodiments described herein in the description and the claims optionally in combination with conventional excipients and/or carriers.

In a further embodiment, the invention relates to pharmaceutical preparation comprising a compound of general formula (I) or (Ia) according to anyone of the embodiments described herein in the description and the claims—or one of the pharmaceutically acceptable salts thereof—and at least one other cytostatic or cytotoxic active substance, different from formula (I) or (Ia).

The present invention further relates to hydrates, solvates, polymorphs, metabolites, derivatives and prodrugs of compounds of general formula (I) or (Ia).

The present invention further relates to a pharmaceutically acceptable salt of a compound of general formula (I) with anorganic or organic acids or bases.

In another aspect the invention relates to compounds of general formula (I) or (Ia)—or the pharmaceutically acceptable salts thereof—as medicaments.

In another aspect the invention relates to compounds of general formula (I) or (Ia)—or the pharmaceutically acceptable salts thereof—for use in a method for treatment of the human or animal body.

In another aspect the invention relates to compounds of general formula (I) or (Ia)—or the pharmaceutically acceptable salts thereof—for use in the treatment and/or prevention of cancer, infections, inflammations and autoimmune diseases.

In another aspect the invention relates to compounds of general formula (I) or (Ia)—or the pharmaceutically acceptable salts thereof—for use in a method for treatment and/or prevention of cancer, infections, inflammations and autoimmune diseases in the human and animal body.

In another aspect the invention relates to compounds of general formula (I) or (Ia)—or the pharmaceutically acceptable salts thereof—for use in the treatment and/or prevention of cancer.

In another aspect the invention relates to the use of the compounds of general formula (I) or (Ia)—or the pharmaceutically acceptable salts thereof—in the treatment and/or prevention of cancer.

In another aspect the invention relates to compounds of general formula (I) or (Ia)—or the pharmaceutically acceptable salts thereof—for use in a method for treatment and/or prevention of cancer in the human or animal body.

In another aspect the invention relates to compounds of general formula (I) or (Ia)—or the pharmaceutically acceptable salts thereof—for use in the treatment and/or prevention of hematopoietic malignancies, preferably AML, MM.

In another aspect the invention relates to compounds of general formula (I) or (Ia)—or the pharmaceutically acceptable salts thereof—for use in the treatment and/or prevention of solid tumors, preferably to lung, in particular small cell lung cancer (SCLC), liver, colon, brain, thyroid, pancreas, breast, ovary and prostate cancer.

In another aspect the invention relates to a process for the treatment and/or prevention of cancer comprising administering a therapeutically effective amount of a compound of general formula (I) or (Ia)—or one of the pharmaceutically acceptable salts thereof—to a human being.

In another aspect the invention relates to a pharmaceutical preparation containing as active substance one or more compounds of general formula (I) or (Ia)—or the pharmaceutically acceptable salts thereof—optionally in combination with conventional excipients and/or carriers.

In another aspect the invention relates to a pharmaceutical preparation comprising a compound of general formula (I) or (Ia)—or one of the pharmaceutically acceptable salts thereof—and at least one other cytostatic or cytotoxic active substance, different from formula (I) or (Ia).

In another aspect the invention relates to a method for the treatment of cancer in the human or animal body comprising administering a therapeutically effective amount of a compounds of general formula (I) or (Ia)—or the pharmaceutically acceptable salts thereof.

In another aspect the invention relates to a method for the treatment of hematopoietic malignancies, preferably AML, MM in the human or animal body comprising administering a therapeutically effective amount of a compounds of general formula (I) or (Ia)—or the pharmaceutically acceptable salts thereof.

In another aspect the invention relates to a method for the treatment of solid tumors, preferably to lung, in particular small cell lung cancer (SCLC), liver, colon, brain, thyroid, pancreas, breast, ovary and prostate cancer in the human or animal body comprising administering a therapeutically effective amount of a compounds of general formula (I) or (Ia)—or the pharmaceutically acceptable salts thereof.

DEFINITIONS

Terms that are not specifically defined here have the meanings that are apparent to the skilled man in the light of the overall disclosure and the context as a whole.

As used herein, the following definitions apply, unless stated otherwise.

In the groups, radicals, or moieties defined below, the number of carbon atoms is often specified preceding the group, for example, —$C_{1-5}$alkyl means an alkyl group or radical having 1 to 5 carbon atoms. In general, for groups comprising two or more subgroups, the first named subgroup is the radical attachment point, for example the substitutent —$C_{1-5}$ alkyl-$C_{3-10}$cycloalkyl, means a $C_{3-10}$cycloalkyl group which is bound to a $C_{1-5}$alkyl, the latter of which is bound to the core structure or to the group to which the substitutent is attached.

The indication of the number of members in groups that contain one or more heteroatom(s) (heteroalkyl, heteroaryl, heteroarylalkyl, heterocyclyl, heterocycylalkyl) relates to the total atomic number of all the ring members or chain members or the total of all the ring and chain members.

The person skilled in the art will appreciate that substituent groups containing a nitrogen atom can also be indicated as amine or amino. Similarly, groups containing oxygen atom can also be indicated with -oxy, like for example alkoxy. Groups containing —C(O)— can also be indicated as carboxy; groups containing —NC(O)— can also be indicated as amide; groups containing —NC(O)N— can also be indicated as urea; groups containing —NS(O)$_2$— can also be indicated as sulfonamide.

Alkyl denotes monovalent, saturated hydrocarbon chains, which may be present in both linear and branched form. If an alkyl is substituted, the substitution may take place independently of one another, by mono- or polysubstitution in each case, on all the hydrogen-carrying carbon atoms.

The term "$C_{1-5}$-alkyl" includes for example methyl (Me; —CH$_3$), ethyl (Et; —CH$_2$CH$_3$), 1-propyl (n-propyl; n-Pr; —CH$_2$CH$_2$CH$_3$), 2-propyl (i-Pr; iso-propyl; —CH(CH$_3$)$_2$), 1-butyl (n-butyl; n-Bu; —CH$_2$CH$_2$CH$_2$CH$_3$), 2-methyl-1-propyl (iso-butyl; i-Bu; —CH$_2$CH(CH$_3$)$_2$), 2-butyl (sec-butyl; sec-Bu; —CH(CH$_3$)CH$_2$CH$_3$), 2-methyl-2-propyl (tert-butyl; t-Bu; —C(CH$_3$)$_3$), 1-pentyl (n-pentyl; —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 3-methyl-1-butyl (iso-pentyl; —CH$_2$CH$_2$CH(CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 2,2-dimethyl-1-propyl (neo-pentyl; —CH$_2$C(CH$_3$)$_3$), 2-methyl-1-butyl (—CH$_2$CH(CH$_3$)CH$_2$CH$_3$). By the terms propyl, butyl, pentyl, etc. without any further definition are meant saturated hydrocarbon groups with the corresponding number of carbon atoms, wherein all isomeric forms are included.

The above definition for alkyl also applies if alkyl is a part of another group such as for example $C_{x-y}$-alkylamino or $C_{x-y}$-alkyloxy or $C_{x-y}$-alkoxy, wherein $C_{x-y}$-alkyloxy and $C_{x-y}$-alkoxy indicate the same group.

The term alkylene can also be derived from alkyl. Alkylene is bivalent, unlike alkyl, and requires two binding partners. Formally, the second valency is produced by removing a hydrogen atom in an alkyl. Corresponding groups are for example —CH$_3$ and —CH$_2$—, —CH$_2$CH$_3$ and —CH$_2$CH$_2$— or >CHCH$_3$ etc.

The term "$C_{1-4}$-alkylene" includes for example —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C(CH$_3$)$_2$—CH$_2$)—, —(CH(CH$_3$)—CH(CH$_3$))—, —(CH$_2$—CH(CH$_2$CH$_3$))—, —(CH(CH$_2$CH$_3$)—CH$_2$)—, —(CH(CH$_2$CH$_2$CH$_3$))—, —(CHCH(CH$_3$)$_2$)—and —C(CH$_3$)(CH$_2$CH$_3$)—.

Other examples of alkylene are methylene, ethylene, propylene, 1-methylethylene, butylene, 1-methylpropylene, 1.1-dimethylethylene, 1,2-dimethylethylene, pentylene, 1,1-dimethylpropylene, 2,2-dimethylpropylene, 1,2-dimethylpropylene, 1,3-dimethylpropylene, etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene.

The above definition for alkylene also applies if alkylene is part of another group such as for example in HO—$C_{x-y}$-alkylenamino or H$_2$N—$C_{x-y}$-alkylenoxy.

Unlike alkyl, alkenyl consists of at least two carbon atoms, wherein at least two adjacent carbon atoms are joined together by a C═C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl(ethenyl), prop-1-enyl, allyl (prop-2-enyl), isopropenyl, but-1-enyl, but-2-enyl, but-3- enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexadienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another group such as for example in $C_{x-y}$-alkenylamino or $C_{x-y}$-alkenyloxy.

Unlike alkylene, alkenylene consists of at least two carbon atoms, wherein at least two adjacent carbon atoms are joined together by a C—C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another group as in for example HO—$C_{x-y}$-alkenylenamino or $H_2N$—$C_{x-y}$-alkenylenoxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl.

By the generic terms propynyl, butynyl, pentynyl, etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl.

If a hydrocarbon chain carries both at least one double bond and also at least one triple bond, by definition it belongs to the alkynyl subgroup.

The above definition for alkynyl also applies if alkynyl is part of another group, as in $C_{x-y}$-alkynylamino or $C_{x-y}$-alkynyloxy, for example.

Unlike alkylene, alkynylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, etc. without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethylethynylene.

The above definition for alkynylene also applies if alkynylene is part of another group, as in HO—$C_{x-y}$-alkynyleneamino or $H_2N$—$C_{x-y}$-alkynyleneoxy, for example.

By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —CI=$CH_2$, —C≡C—$CF_3$, —$CHFCH_2CH_3$, —$CHFCH_2CF_3$ etc.

From the previously defined haloalkyl (haloalkenyl, haloalkynyl) are also derived the terms haloalkylene (haloalkenylene, haloalkynylene). Haloalkylene (haloalkenyl, haloalkynyl), unlike haloalkyl, is bivalent and requires two binding partners. Formally, the second valency is formed by removing a hydrogen atom from a haloalkyl.

Corresponding groups are for example —$CH_2F$ and —CHF—, —$CHCH_2F$ and —CHFCHF— or >$CFCH_2F$ etc.

The above definitions also apply if the corresponding halogen groups are part of another group.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms together. In spiro-hydrocarbon rings a carbon atom (spiroatom) belongs to two rings together. If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl(octahydroindenyl), bicyclo[4.4.0]decyl(decahydronaphthalene), bicyclo[2.2.1]heptyl(norbornyl), bicyclo[4.1.0]heptyl(norcaranyl), bicyclo-[3.1.1]heptyl (pinanyl), spiro[2.5]octyl, spiro[3.3]heptyl etc.

The above definition for cycloalkyl also applies if cycloalkyl is part of another group as in $C_{x-y}$-cycloalkylamino or $C_{x-y}$-cycloalkyloxy, for example.

If the free valency of a cycloalkyl is saturated, then an alicyclic group is obtained.

The term cycloalkylene can thus be derived from the previously defined cycloalkyl. Cycloalkylene, unlike cycloalkyl, is bivalent and requires two binding partners. Formally, the second valency is obtained by removing a hydrogen atom from a cycloalkyl. Corresponding groups are for example cyclohexyl and

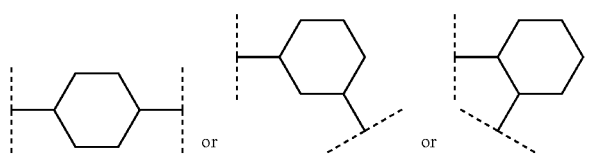

(cyclohexylene).

The above definition for cycloalkylene also applies if cycloalkylene is part of another group as in HO—$C_{x-y}$-cycloalkyleneamino or $H_2N$—$C_{x-y}$-cycloalkyleneoxy, for example.

Cycloalkenyl is also made up of the subgroups monocyclic hydrocarbon rings, bicyclic hydrocarbon rings and spiro-hydrocarbon rings. However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained. If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl(norborna-2,5-dienyl), bicyclo[2.2.1]hept-2-enyl(norbornenyl), spiro[4.5]dec-2-ene etc.

The above definition for cycloalkenyl also applies when cycloalkenyl is part of another group as in $C_{x-y}$-cycloalkenylamino or $C_{x-y}$-cycloalkenyloxy, for example.

If the free valency of a cycloalkenyl is saturated, then an unsaturated alicyclic group is obtained.

The term cycloalkenylene can thus be derived from the previously defined cycloalkenyl. Cycloalkenylene, unlike cycloalkenyl, is bivalent and requires two binding partners. Formally the second valency is obtained by removing a hydrogen atom from a cycloalkenyl. Corresponding groups are for example cyclopentenyl and

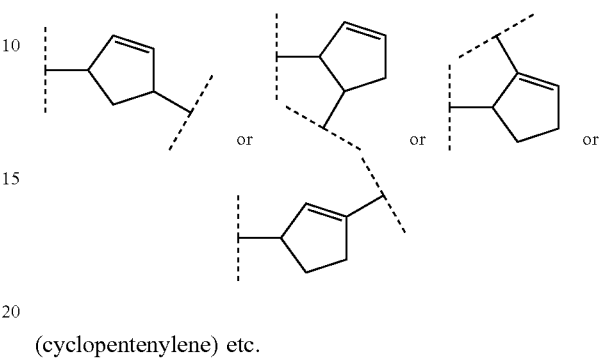

(cyclopentenylene) etc.

The above definition for cycloalkenylene also applies when cycloalkenylene is part of another group as in HO—$C_{x-y}$-cycloalkenyleneamino or $H_2N$—$C_{x-y}$-cycloalkenyleneoxy, for example.

Aryl denotes a mono-, bi- or tricyclic group with at least one aromatic carbocycle. Preferably it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be saturated or partially saturated. If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl(2,3-dihydroindenyl), indenyl, anthracenyl, phenanthrenyl, tetrahydronaphthyl(1,2,3,4-tetrahydronaphthyl, tetralinyl), dihydronaphthyl(1,2-dihydronaphthyl), fluorenyl etc.

The above definition of aryl also applies when aryl is part of another group as in arylamino or aryloxy, for example.

If the free valency of an aryl is saturated, then an aromatic group is obtained.

The term arylene can also be derived from the previously defined aryl. Arylene, unlike aryl, is bivalent and requires two binding partners. Formally, the second valency is formed by removing a hydrogen atom from an aryl. Corresponding groups are e.g. phenyl and

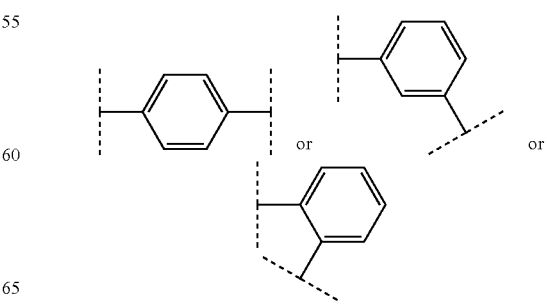

(o, m, p-phenylene), naphthyl and

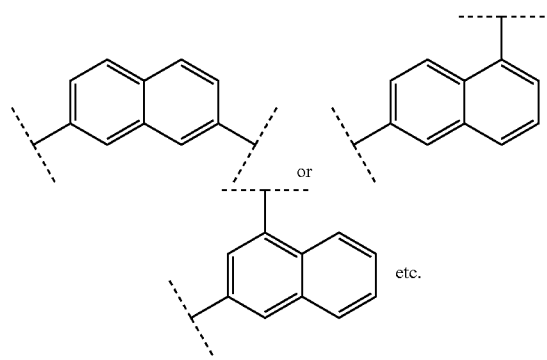

etc.

The above definition for arylene also applies when arylene is part of another group as in HO-aryleneamino or H₂N-aryleneoxy for example.

Heterocyclyl denotes ring systems, which are derived from the previously defined cycloalkyl, cycloalkenyl and aryl by replacing one or more of the groups —CH$_2$-independently of one another in the hydrocarbon rings by the groups —O—, —S— or —NH— or by replacing one or more of the groups =CH— by the group =N—, wherein a total of not more than five heteroatoms may be present, at least one carbon atom may be present between two oxygen atoms and between two sulphur atoms or between one oxygen and one sulphur atom and the ring as a whole must have chemical stability. Heteroatoms may optionally be present in all the possible oxidation stages (sulphur→sulphoxide —SO, sulphone —SO$_2$—; nitrogen→N-oxide).

A direct result of the derivation from cycloalkyl, cycloalkenyl and aryl is that heterocyclyl is made up of the subgroups monocyclic heterorings, bicyclic heterorings, tricyclic heterorings and spiro-heterorings, which may be present in saturated or unsaturated form. Saturated and unsaturated, non aromatic, heterocyclyl are also defined as heterocycloalkyl. By unsaturated is meant that there is at least one double bond in the ring system in question, but no heteroaromatic system is formed. In bicyclic heterorings two rings are linked together so that they have at least two (hetero)atoms in common. In spiro-heterorings a carbon atom (spiroatom) belongs to two rings together. If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system. When the heterocyclyl has a nitrogen atom, the preferred position to bind the heterocyclyl substituent to the molecule is the nitrogen atom.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, 1,3-dioxolanyl, tetrahydropyranyl, tetrahydrothiopyranyl, [1.4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S, S-dioxide, homothiomorpholinyl-S-oxide, 2,3-dihydroazet, 2H-pyrrolyl, 4H-pyranyl, 1,4-dihydropyridinyl, 8-azabicyclo[3.2.1]octyl, 8-azabicyclo[5.1.0]octyl, 2-oxa-5-azabicyclo[2.2.1]-heptyl, 8-oxa-3-aza-bicyclo[3.2.1]octyl, 3,8-diaza-bicyclo[3.2.1]octyl, 2,5-diaza-bicyclo-[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, 1,4-dioxa-spiro[4.5]-decyl, 1-oxa-3.8-diaza-spiro[4.5]decyl, 2,6-diaza-spiro[3.3]heptyl, 2,7-diaza-spiro[4.4]nonyl, 2,6-diaza-spiro[3.4]octyl, 3,9-di-aza-spiro[5.5]undecyl, 2.8-diaza-spiro[4.5]decyl etc.

Further examples are the structures illustrated below, which may be attached via each hydrogen-carrying atom (exchanged for hydrogen):

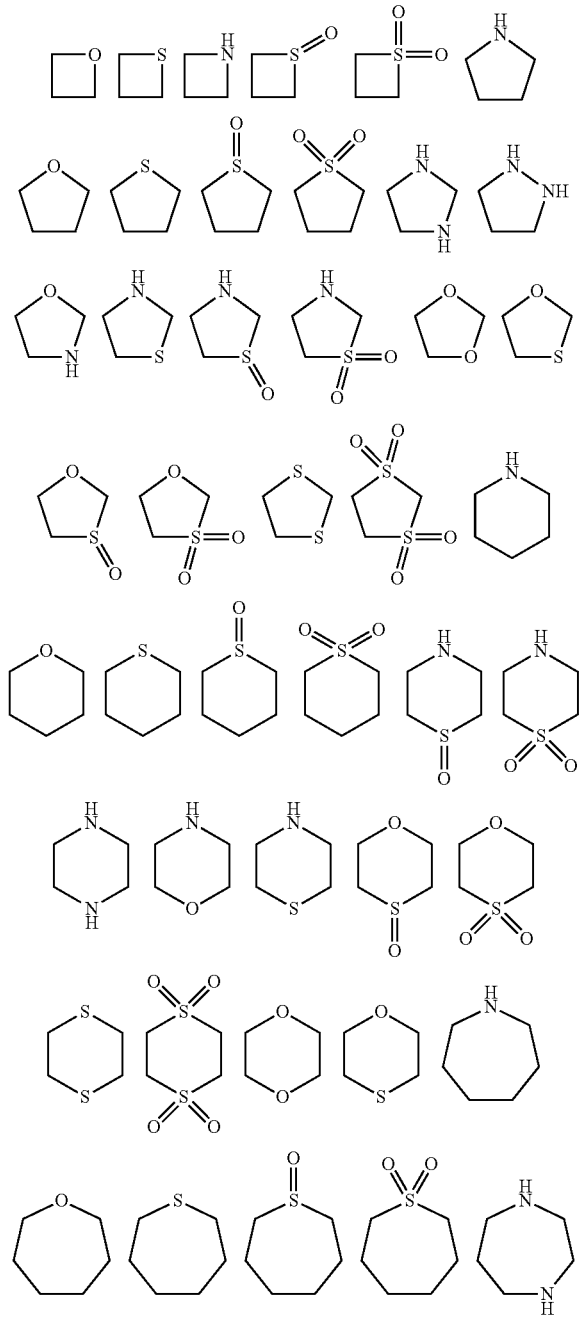

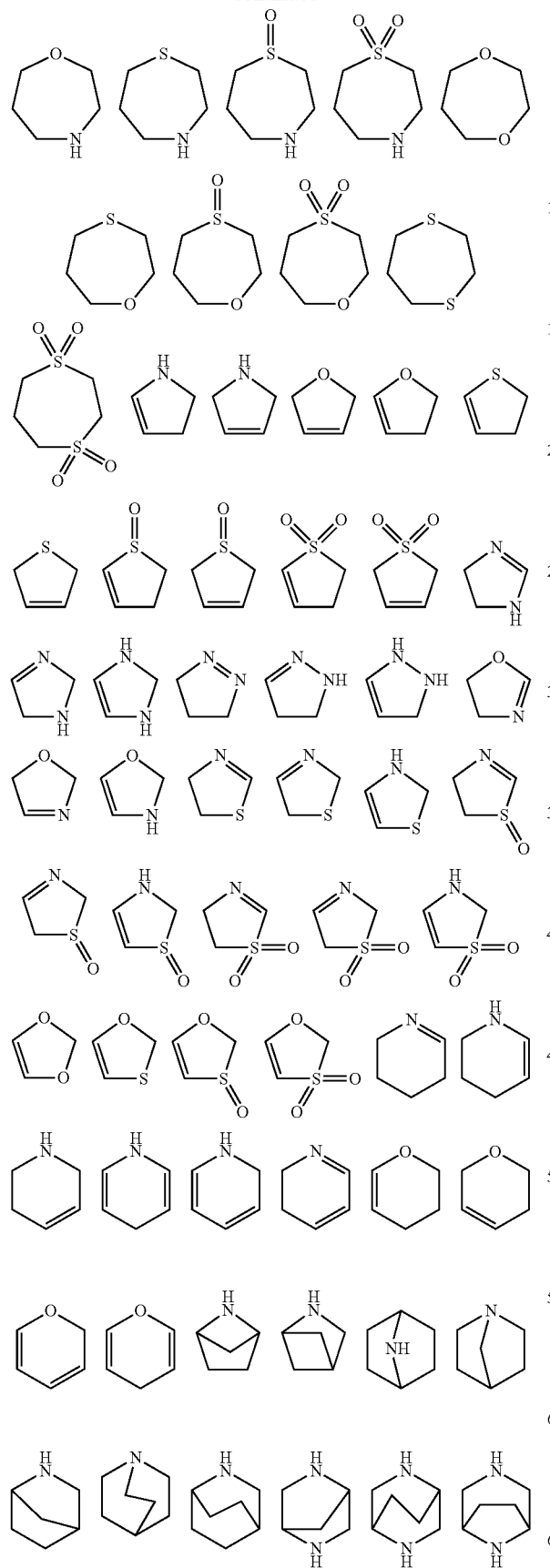
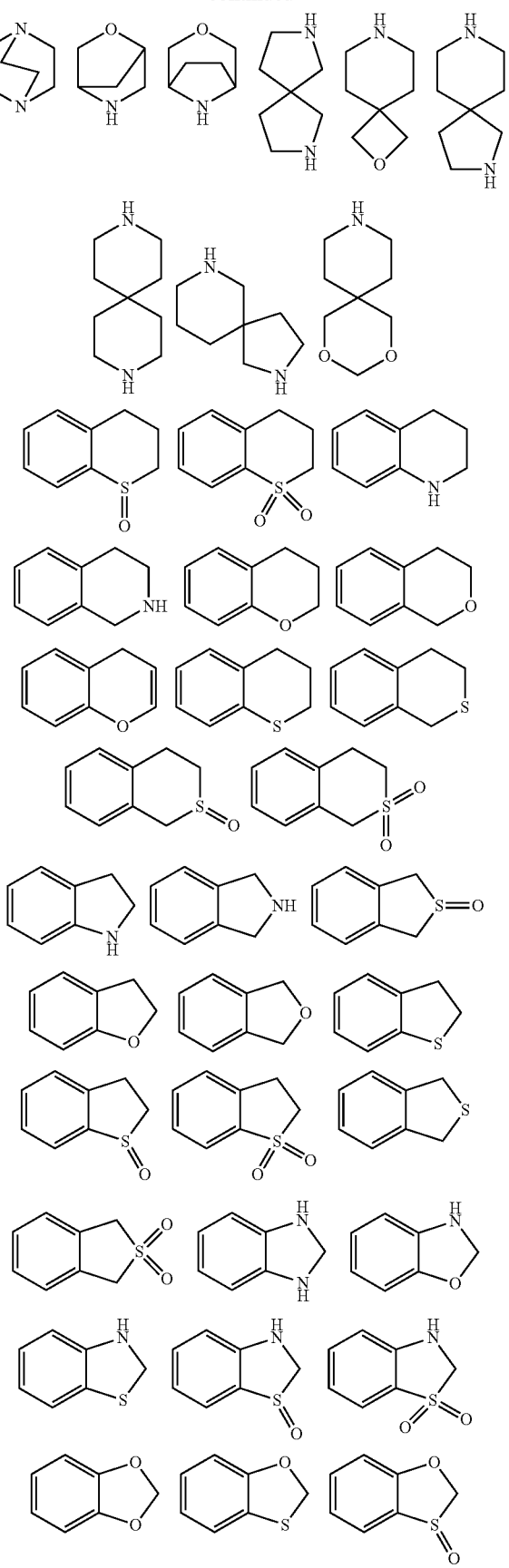

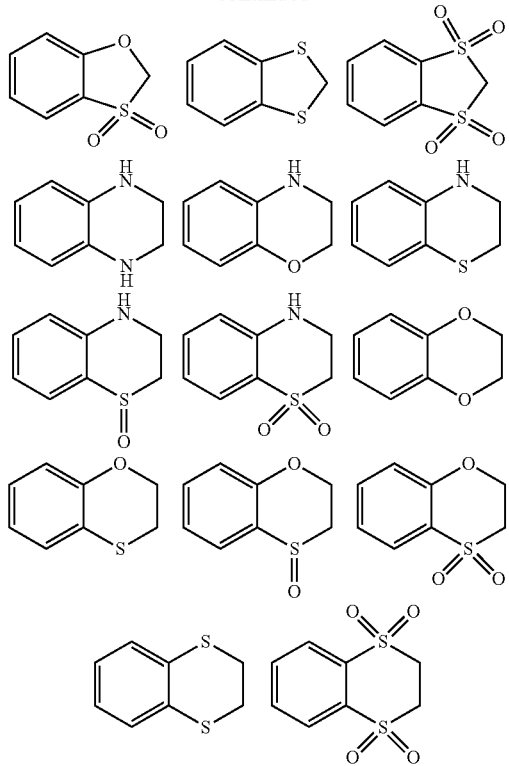

The above definition of heterocyclyl also applies if heterocyclyl is part of another group as in heterocyclylamino or heterocyclyloxy for example.

If the free valency of a heteroyclyl is saturated, then a heterocyclic group is obtained.

The term heterocyclylene is also derived from the previously defined heterocyclyl. Heterocyclylene, unlike heterocyclyl, is bivalent and requires two binding partners. Formally, the second valency is obtained by removing a hydrogen atom from a heterocyclyl. Corresponding groups are for example piperidinyl and

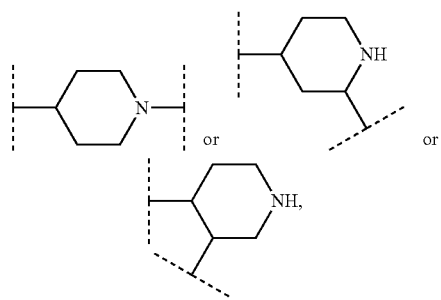

2,3-dihydro-1H-pyrrolyl and

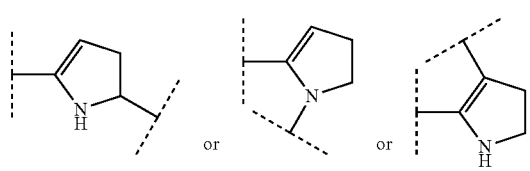

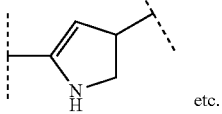

The above definition of heterocyclylene also applies if heterocyclylene is part of another group as in HO-heterocyclyleneamino or $H_2N$-heterocyclyleneoxy for example.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system. If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N-oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, purinyl, pteridinyl, benzothiazolyl, imidazopyridyl, imidazothiazolyl, quinolinyl-N-oxide, indolyl-N-oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

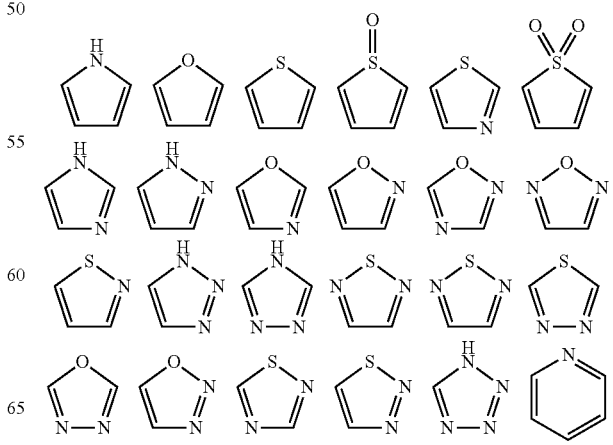

-continued

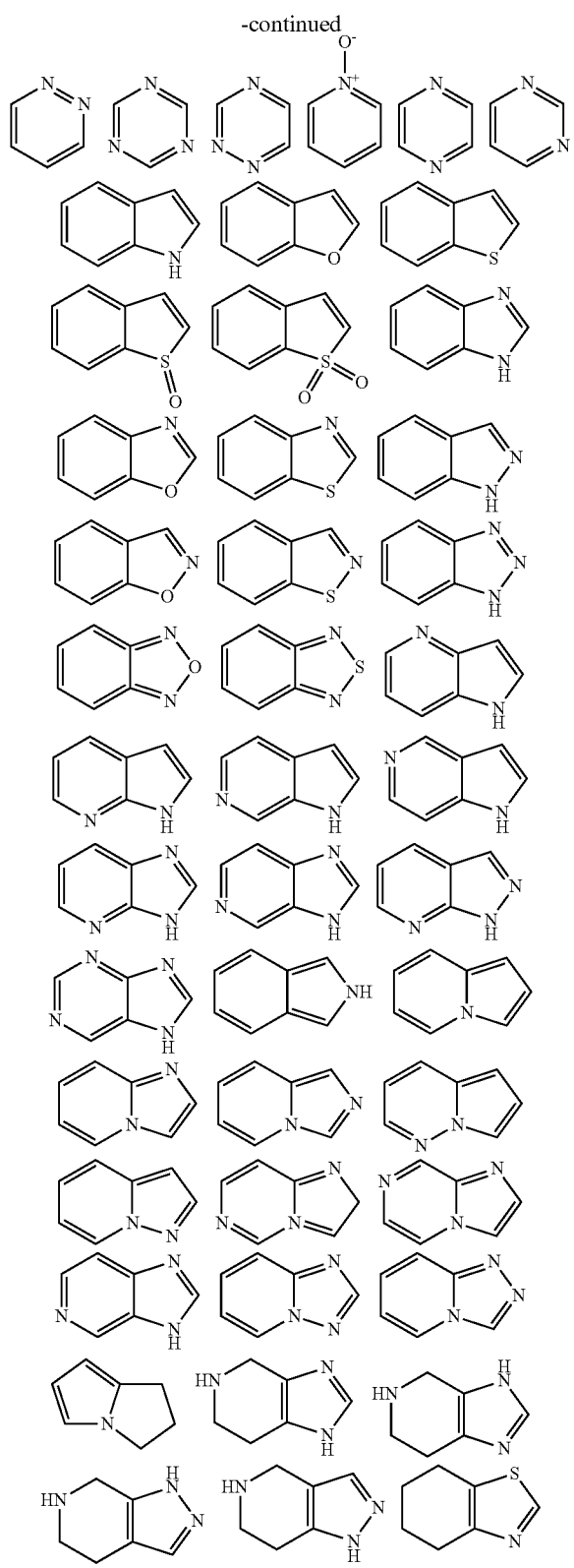

The above definition of heteroaryl also applies when heteroaryl is part of another group as in heteroarylamino or heteroaryloxy, for example.

If the free valency of a heteroaryl is saturated, a heteroaromatic group is obtained.

The term heteroarylene can therefore be derived from the previously defined heteroaryl. Heteroarylene, unlike heteroaryl, is bivalent and requires two binding partners. Formally, the second valency is obtained by removing a hydrogen atom from a heteroaryl. Corresponding groups are for example pyrrolyl and

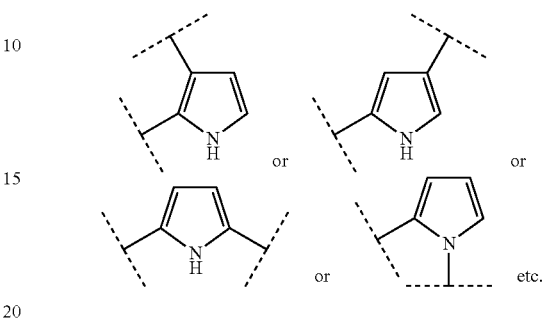

The above definition of heteroarylene also applies when heteroarylene is part of another group as in HO-heteroaryleneamino or $H_2N$-heteroaryleneoxy, for example.

The bivalent groups mentioned above (alkylene, alkenylene, alkynylene etc.) may also be part of composite groups (e.g. $H_2N$—$C_{1-4}$alkylene- or HO—$C_{1-4}$alkylene-). In this case one of the valencies is saturated by the attached group (here: —$NH_2$, —OH), so that a composite group of this kind written in this way is only a monovalent substituent over all.

By substituted is meant that a hydrogen atom which is bound directly to the atom under consideration, is replaced by another atom or another group of atoms (substituent). Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, =$N_2$ or the like, may only be substituted at carbon atoms, wherein the bivalent substituent =O may also be a substituent at sulphur. Generally, substitution may be carried out by a bivalent substituent only at ring systems and requires replacement by two geminal hydrogen atoms, i.e. hydrogen atoms that are bound to the same carbon atom that is saturated prior to the substitution. Substitution by a bivalent substituent is therefore only possible at the group —$CH_2$— or sulphur atoms of a ring system.

Stereochemistry/Solvates/Hydrates: Unless stated otherwise a structural formula given in the description or in the claims or a chemical name refers to the corresponding compound itself, but also encompasses the tautomers, stereoisomers, optical and geometric isomers (e.g. enantiomers, diastereomers, E/Z isomers, etc.), racemates, mixtures of separate enantiomers in any desired combinations, mixtures of diastereomers, mixtures of the forms mentioned hereinbefore (if such forms exist) as well as salts, particularly pharmaceutically acceptable salts thereof. The compounds and salts according to the invention may be present in solvated form (e.g. with pharmaceutically acceptable solvents such as e.g. water, ethanol etc.) or in unsolvated form. Generally, for the purposes of the present invention the solvated forms, e.g. hydrates, are to be regarded as of equal value to the unsolvated forms.

Salts: The term "pharmaceutically acceptable" is used herein to denote compounds, materials, compositions and/or formulations which are suitable, according to generally recognised medical opinion, for use in conjunction with human and/or animal tissue and do not have or give rise to any excessive toxicity, irritation or immune response or lead to other problems or complications, i.e. correspond overall to an acceptable risk/benefit ratio.

The term "pharmaceutically acceptable salts" relates to derivatives of the chemical compounds disclosed in which the parent compound is modified by the addition of acid or base. Examples of pharmaceutically acceptable salts include (without being restricted thereto) salts of mineral or organic acids in relation to basic functional groups such as for example amines, alkali metal or organic salts of acid functional groups such as for example carboxylic acids, etc. These salts include in particular acetate, ascorbate, benzenesulphonate, benzoate, besylate, bicarbonate, bitartrate, bromide/hydrobromide, Ca-edetate/edetate, camsylate, carbonate, chloride/hydrochloride, citrate, edisylate, ethane disulphonate, estolate, esylate, fumarate, gluceptate, gluconate, glutamate, glycolate, glycollylarsnilate, hexylresorcinate, hydrabamine, hydroxymaleate, hydroxynaphthoate, iodide, isothionate, lactate, lactobionate, malate, maleate, mandelate, methanesulphonate, mesylate, methylbromide, methylnitrate, methylsulphate, mucate, napsylate, nitrate, oxalate, pamoate, pantothenate, phenyl acetate, phosphate/diphosphate, polygalacturonate, propionate, salicylate, stearate, subacetate, succinate, sulphamide, sulphate, tannate, tartrate, teoclate, toluenesulphonate, triethiodide, ammonium, benzathine, chloroprocaine, choline, diethanolamine, ethylenediamine, meglumin and procaine. Other pharmaceutically acceptable salts may be formed with cations of metals such as aluminium, calcium, lithium, magnesium, potassium, sodium, zinc, etc. (cf. also Pharmaceutical salts, Birge, S. M. et al., J. Pharm. Sci., (1977), 66, 1-19).

The pharmaceutically acceptable salts of the present invention may be prepared starting from the parent compound which carries a basic or acidic functionality, by conventional chemical methods. Generally, such salts may be synthesised by reacting the free acid or base form of these compounds with a sufficient amount of the corresponding base or acid in water or an organic solvent such as for example ether, ethyl acetate, ethanol, isopropanol, acetonitrile (or mixtures thereof).

Salts of acids other than those mentioned above, which are useful for example for purifying or isolating the compounds from the reaction mixtures (e.g. trifluoroacetates), are also to be regarded as part of the invention.

In a representation such as for example

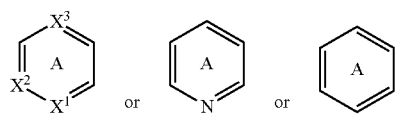

the letter A has the function of a ring designation in order to make it easier, for example, to indicate the attachment of the ring in question to other rings.

For bivalent groups in which it is crucial to determine which adjacent groups they bind and with which valency, the corresponding binding partners are indicated in brackets, where necessary for clarification purposes, as in the following representations:

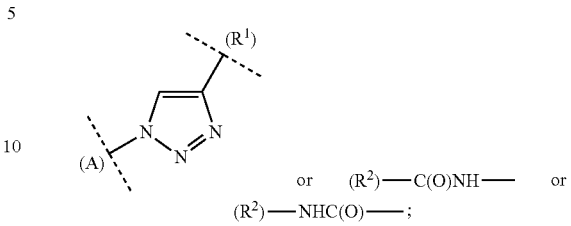

Groups or substituents are frequently selected from among a number of alternative groups/substituents with a corresponding group designation (e.g. $R^a$, $R^b$ etc). If such a group is used repeatedly to define a compound according to the invention in different molecular parts, it must always be borne in mind that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

| List of abbreviations | |
|---|---|
| ACN, CH$_3$CN | acetonitrile |
| Boc | tert.butoxy carbonyl |
| DCM | dichloromethane |
| DIPEA | diisopropylethyl amine |
| DMAP | dimethyl-pyridin-4-yl-amine |
| DMF | N,N-dimethylformamide |
| DMSO | dimethylsulphoxide |
| EDTA | ethylenediaminetetraacetic acid |
| EtOAc or EA | ethyl acetate |
| FCS | Fetal calf serum |
| h | hour(s) |
| HATU | N-[(dimethylamino)-(1H-1,2,3-triazolo[4,5-b]pyridin-1-yl)-methylene]-N-methylmethan-aminium hexafluorophosphate N-oxide |
| HPLC | high performance liquid chromatography |
| KOAc | potassium acetate |
| LiHMDS | lithium hexamethyl disilazide |
| M | Molar |
| Min | minute(s) |
| mL | Milliliter |
| MS | mass spectrometry |
| N | Normal |
| NMR | nuclear resonance spectroscopy |
| PE | petrol ether |
| PPh3 | triphenylphosphine |
| DIBAL | diisobutylaluminium hydride |
| RP | reversed phase |
| Rpm | rounds per minute |
| RT or rt | room temperature |
| STAB | Sodium triacetoxy borohydride |
| TBME | tert.butyl methyl ether |
| TEA | triethylamine |
| tert | tertiary |
| TFA | trifluoroacetic acid |
| THF | tetrahydrofuran |
| tR | retention time [min] |
| TRIS | tris(hydroxymethyl)aminomethane |
| wt % | weight percent |
| sat. | Saturated |
| Ar | aromatic |

Other features and advantages of the present invention will become apparent from the following more detailed Examples which exemplarily illustrate the principles of the invention without restricting its scope.

GENERAL

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

The compounds are named according to the Beilstein rules using the Autonom software (Beilstein). If a compound is to be represented both by a structural formula and by its nomenclature, in the event of a conflict the structural formula is decisive.

Chromatography

Thin layer chromatography is carried out on ready-made TLC plates of silica gel 60 on glass (with fluorescence indicator F-254) made by Merck.

The preparative high pressure chromatography (HPLC) of the example compounds according to the invention is carried out with columns made by Waters (names: Sunfire C18 OBD, 10 μm, 30×100 mm Part. No. 186003971; X-Bridge C18 OBD, 10 μm, 30×100 mm Part. No. 186003930). The compounds are eluted using different gradients of $H_2O$/ACN wherein 0.2% HCOOH is added to the water (acid conditions). For chromatography under basic conditions the water is made basic according to the following recipe: 5 mL of ammonium hydrogen carbonate solution (158 g to 1 L $H_2O$) and 2 ml 32% ammonia$_{(aq)}$ are made up to 1 L with $H_2O$.

The analytical HPLC (reaction monitoring) of intermediate compounds is carried out with columns made by Waters and Phenomenex. The analytical equipment is also provided with a mass detector in each case.

HPLC Mass Spectroscopy/UV Spectrometry

The retention times/MS-ESI$^+$ for characterising the example compounds according to the invention are produced using an HPLC-MS apparatus (high performance liquid chromatography with mass detector) made by Agilent. Compounds that elute at the injection peak are given the retention time $t_{Ret.}$=0.

HPLC-Methods Preparative
Prep. HPLC1
  HPLC: 333 and 334 Pumps
  Column: Waters X-Bridge C18 OBD, 10 μm, 30×100 mm,
    Part. No. 186003930
  Solvent: A: 10 mM $NH_4HCO_3$ in $H_2O$; B: Acetonitril (HPLC grade)
  Detection: UV/Vis-155
  Flow: 50 ml/min
  Gradient: 0.00-1.50 min: 1.5% B
    1.50-7.50 min: varying
    7.50-9.00 min: 100% B
Prep. HPLC2
  HPLC: 333 and 334 Pumps
  Column: Waters Sunfire C18 OBD, 10 μm, 30×100 mm, Part. No. 186003971
  Solvent: A: $H_2O$+0.2% HCOOH; B: Acetonitril (HPLC grade)+0.2% HCOOH
  Detection: UV/Vis-155
  Flow: 50 ml/min
  Gradient: 0.00-1.50 min: 1.5% B
    1.50-7.50 min: varying
    7.50-9.00 min: 100% B HPLC-Methods Analytic
LCMSBAS1
  HPLC: Agilent 1100 Series
  MS: Agilent LC/MSD SL
  Column: Phenomenex Mercury Gemini C18, 3 μm, 2×20 mm,
    Part. No. 00M-4439-B0-CE
  Solvent: A: 5 mM $NH_4HCO_3$/20 mM $NH_3$ in $H_2O$; B: Acetonitril (HPLC grade)
  Detection: MS: Positive and negative mode
  Mass range: 120-900 m/z
  Flow: 1.00 ml/min
  Column temperature: 40° C.
  Gradient: 0.00-2.50 min: 5%→95% B
    2.50-2.80 min: 95% B
    2.81-3.10 min: 95%→5% B
FECB5
  HPLC: Agilent 1100/1200 Series
  MS: Agilent LC/MSD SL
  Column: Waters X-Bridge C18 OBD, 5 μm, 2.1×50 mm
  Solvent: A: 5 mM $NH_4HCO_3$/19 mM $NH_3$ in $H_2O$; B: Acetonitril (HPLC grade)
  Detection: MS: Positive and negative mode
  Mass range: 105-1200 m/z
  Flow: 1.20 ml/min
  Column temperature: 35° C.
  Gradient: 0.00-1.25 min: 5%→95% B
    1.25-2.00 min: 95% B
    2.00-2.01 min: 95%→5% B
FECBM3ESI
  HPLC: Agilent 1100/1200 Series
  MS: Agilent LC/MSD SL
  Column: Waters X-Bridge C18 OBD, 5 μm, 2.1×50 mm
  Solvent: A: 5 mM $NH_4HCO_3$/19 mM $NH_3$ in $H_2O$; B: Acetonitril (HPLC grade)
  Detection: MS: Multimode ESI Positive and negative mode
  Mass range: 105-1200 m/z
  Flow: 1.20 ml/min
  Column temperature: 35° C.
  Gradient: 0.00-1.25 min: 5%→100% B
    1.25-2.00 min: 100% B
    2.00-2.01 min: 100% 5% B
VAB
  HPLC: Agilent 1100/1200 Series
  MS: Agilent LC/MSD SL
  Column: Waters X-Bridge BEH C18, 2.5 μm, 2.1×30 mm XP
  Solvent: A: 5 mM $NH_4HCO_3$/19 mM $NH_3$ in $H_2O$; B: Acetonitril (HPLC grade)
  Detection: MS: Positive and negative mode
  Mass range: 100-1200 m/z
  Flow: 1.40 ml/min
  Column temperature: 45° C.
  Gradient: 0.00-1.00 min: 5%→100% B
    1.00-1.37 min: 100% B
    1.37-1.40 min: 100%→5% B
FA-8
  HPLC-MS: Waters—Alliance 2996
  Column: Symmetryshield C18, 5 μm, 4.6×250 mm
  Solvent: A: $H_2O$+0.1% TFA; B: Acetonitril (HPLC grade)
  Detection: MS: Positive and negative mode
  Mass range: 100-1200 m/z
  Flow: 1.00 ml/min
  Column temperature: 25° C.
  Gradient: 2.00-8.00 min: 20%→80% B
    8.00-19.00 min: 80% B
    19.00-20.00 min: 80%→20% B FSUN2
 HPLC: Agilent 1100/1200 Series
 MS: Agilent LC/MSD SL
 Column: Waters Sunfire C18, 5 μm, 2.1×50 mm
 Solvent: A: H₂O+0.2% formic acid; B: Acetonitril (HPLC grade)
 Detection: MS: Positive and negative mode
 Mass range: 105-1200 m/z
 Flow: 1.20 ml/min
 Column temperature: 35° C.
 Gradient: 0.0 min: 5% B
  0.0-1.50 min: 5%→95% B
  1.50-2.00 min: 95% B
  2.00-2.01 min: 95%→5% B Preparation of the Compounds According to the Invention The compounds according to the invention are prepared by the methods of synthesis described hereinafter, in which the substituents of the general formula have the meanings given hereinbefore. These methods are intended as an illustration of the invention, without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

Unless otherwise specified, the substituents R1 through R3 of the following reaction schemes are as defined in the description and claims.

The synthesis of key intermediate J from starting material A is illustrated in Scheme 1.

Starting from A, a nucleophilic aromatic substitution reaction can be used to introduce hydrazine B, which leads to C. Compound G can be synthesized applying an amidation reaction with D followed by a bromation with F. After cleavage of the amide and ring closer with an orthoester derivative I the central intermediate J can be obtained.

The synthesis of compounds of formula I-III from key intermediate J is illustrated in Scheme 2.

Scheme 2

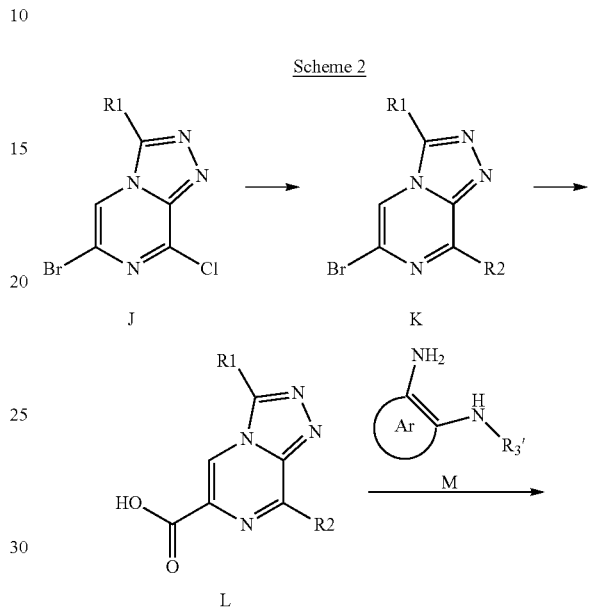

Scheme 1

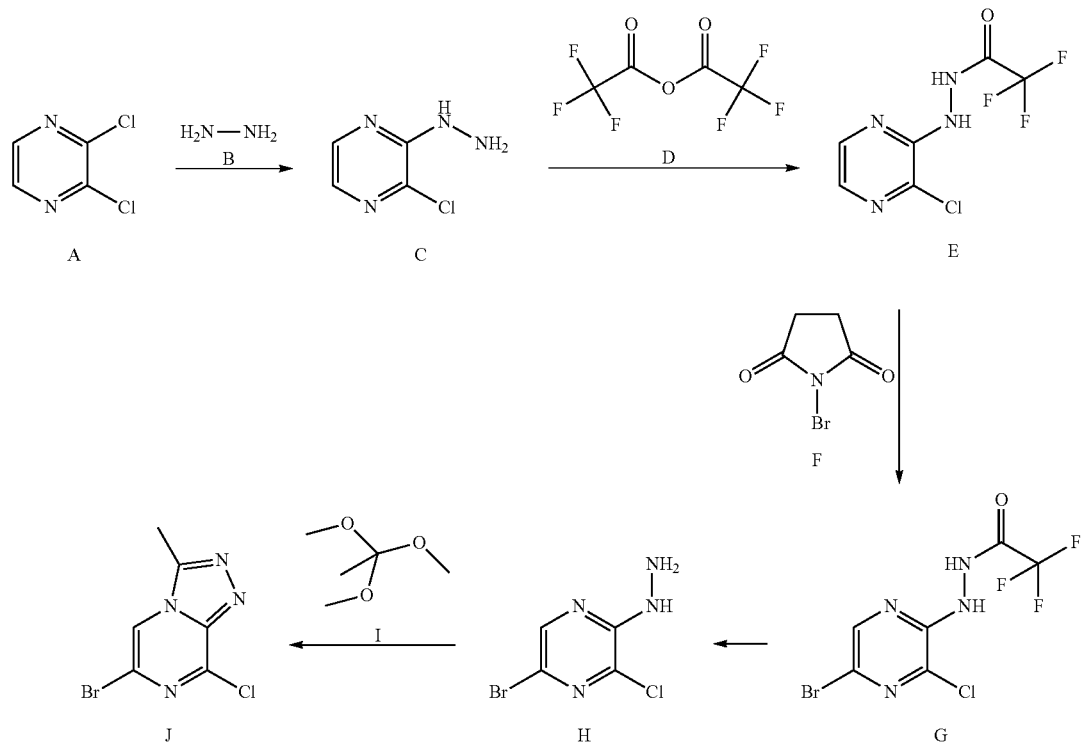

-continued

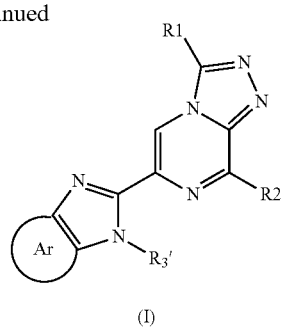

(I)

Residue R2 can be introduced via a nucleophilic aromatic substitution reaction using the corresponding amine, alcohol, thiol or a carbo nucleophile (e.g. diethylmalonate) to produce intermediate K.

Intermediate M, which is synthesized from K using a palladium catalyzed carbonylation reaction, is the central intermediate for final compounds I.

Intermediate M was condensed with aromatic/heteroaromatic diamines Q resulting in final compounds I.

Preparation of Intermediate J-1

6-bromo-8-chloro-3-methyl-[1,2,4]triazolo[4,3-a]pyrazine J-1

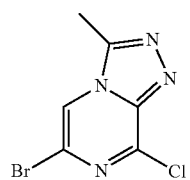

Reaction scheme:

2-chloro-3-hydrazinylpyrazine C-1

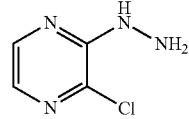

2,3-Dichloropyrazine A-1 (15 g; 100.68 mmol) and hydrazine hydrate 65% (15.509 ml; 201.37 mmol) are dissolved in 45 ml ethanol and stirred for 1 h at 80° C. While cooling down, a precipitate is formed. It is slurred up with a small amount of water and filtered off. It is washed with water and then dried to afford the product.

Yield: 93% (13.6 g; 94.07 mmol)

HPLC-MS: $(M+H)^+=145/147$; $t_{Ret}=0.34$ min; method FECB5

N'-(3-chloropyrazin-2-yl)-2,2,2-trifluoroacetohydrazide E-1

2-Chloro-3-hydrazinylpyrazine C-1 (15.6 g; 108 mmol) is slurried up in (300 ml) THF and cooled down in an ice bath

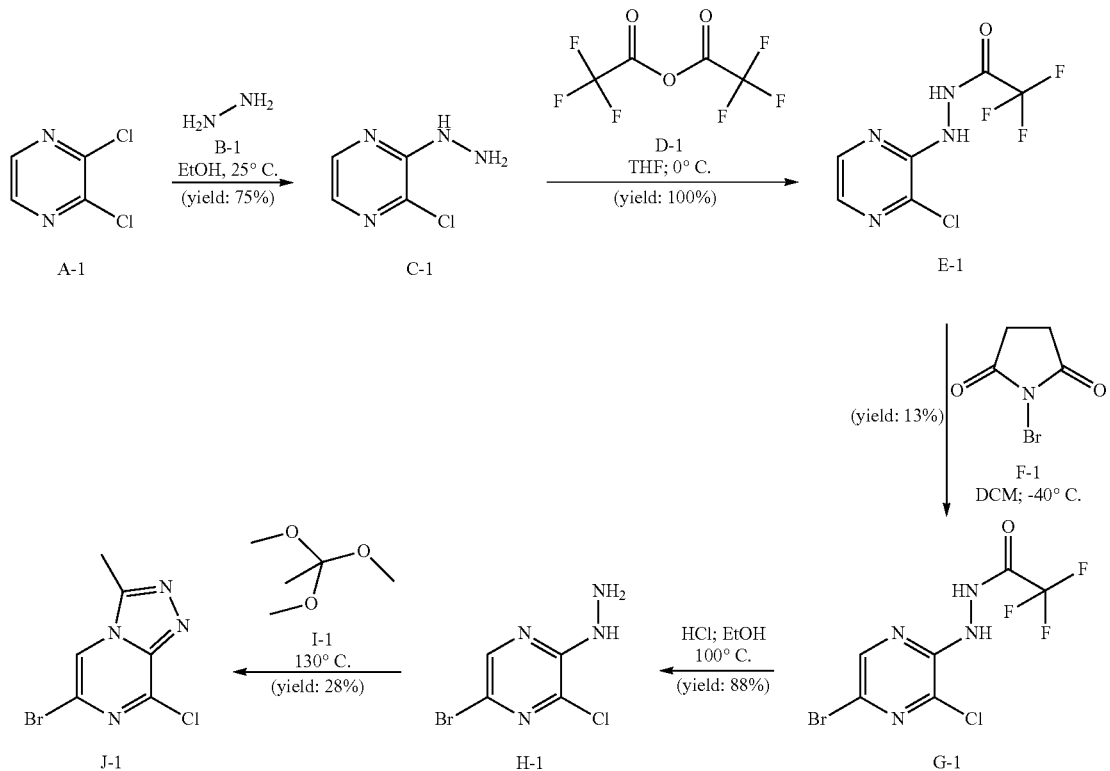

to −5° C. Trifluoroacetic anhydride (17 ml; 118 mmol) is also dissolved in 300 ml THF and dropped slowly to the first solution. After 1 h most of the THF is evaporated, than a small amount of water is added and the mixture is extracted with DCM. The organic phase is dried over MgSO4 and evaporated to dryness.

Yield: 100%

HPLC-MS: (M+H)$^+$=241/243; $t_{Ret}$=1.31 min; method FSUN2

N'-(5-bromo-3-chloropyrazin-2-yl)-2,2,2-trifluoroacetohydrazide G-1

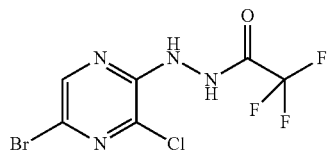 [SMILES: O=C(NNc1ncc(Br)nc1Cl)C(F)(F)F]

N'-(3-chloropyrazin-2-yl)-2,2,2-trifluoroacetohydrazide E-1 (19.5 g; 81.1 mmol) is dissolved in 300 ml anhydrous DCM and cooled down to −40° C. Afterwards NBS (18.8 g; 105 mmol) is added and stirred for 1 hour. The solution is diluted with water and extracted with DCM. The organic phase is then purified with flash chromatography: cHex/(EtOAc/CH3COOH=9/1)=80%/20% to 70%/30% within 10 column volumes.

Yield: 11% (2.83 g; 8.859 mmol)

HPLC-MS: (M−H)$^-$=317/319/321; $t_{Ret}$=1.79 min; method FSUN2

5-bromo-3-chloro-2-hydrazinylpyrazine H-1

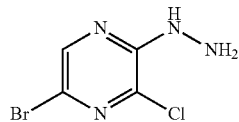

N'-(5-bromo-3-chloropyrazin-2-yl)-2,2,2-trifluoroacetohydrazide G-1 (1.59 g; 4.97 mmol) is dissolved in 30 ml EtOH and treated with 3 ml conc. HCl. It is stirred for 2 hours at 100° C. The reaction mixture is cooled down, diluted with water and then the pH adjusted to 8 with saturated NaHCO3 solution. The water phase is extracted with EtOAc, the organic layer dried over MgSO4 and evaporated to dryness.

Yield: 71% (945 mg; 3.51 mmol)

HPLC-MS: (M−H)$^-$=221/223/225; $t_{Ret}$=1.32 min; method FECB5

6-bromo-8-chloro-3-methyl-[1,2,4]triazolo[4,3-a]pyrazine J-1

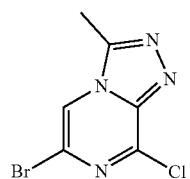

5-bromo-3-chloro-2-hydrazinylpyrazine 11-1 (945 mg; 3.51 mmol) is dissolved in 12 ml trimethyl orthoacetate and heated up to 130° C. for 1 hour. The solution is diluted with water and extracted with EtOAc. The organic phase is then purified with flash chromatography: cHex/EtOAc=70%/30% to 55%/45% within 10 column volumes.

Yield: 71% (824 mg; 3.33 mmol)

HPLC-MS: (M+H)$^+$=247/249/251; $t_{Ret}$=1.23 min; method FECB5

Preparation of Intermediate K-1

6-bromo-3-methyl-N-(propan-2-yl)-[1,2,4]triazolo[4,3-a]pyrazin-8-amine K1

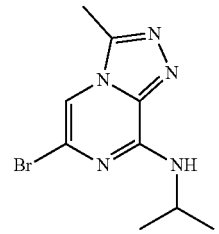

6-bromo-8-chloro-3-methyl-[1,2,4]triazolo[4,3-a]pyrazine J-1 (30.00 g; 121.2 mmol), isopropylamine (14.30 g; 242.44 mmol) and hünigbase (17.20 g; 133.33 mmol) are dissolved in 150 ml NMP and are stirred for 2 hours at 80° C. The reaction mixture is diluted with water and extracted with EtOAc. The organic layer is separated and dried over MgSO$_4$ and evaporated to dryness.

Yield: 70% (42.00 g; 155.55 mmol)

HPLC-MS: (M+H)$^+$=270/272; $t_{Ret}$=0.69 min; method VAB

According to the procedures of K-1 the intermediate K-2-K-5 is synthesized.

| # | Structure | MS (M + H)$^+$; $t_{Ret.}$ HPLC [min] | HPLC-Method |
|---|-----------|---------------------------------------|-------------|
| K-1 | 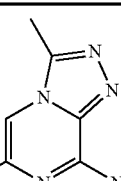 | M + H = 270/272; $t_{Ret.}$ = 0.69 | VAB |
| K-2 | 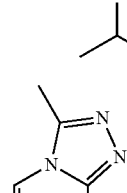 | M + H = 242/244; $t_{Ret.}$ = 0.59 | VAB |

-continued

| # | Structure | MS (M + H)+; $t_{Ret.}$ HPLC [min] | HPLC-Method |
|---|---|---|---|
| K-3 | 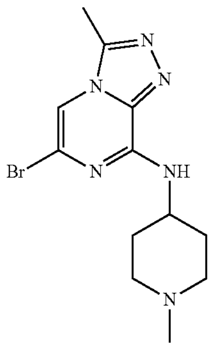 [SMILES: Cc1nnc2c(NC3CCN(C)CC3)nc(Br)cn12] | M + H = 325/327 | VAB |
| K-4 | 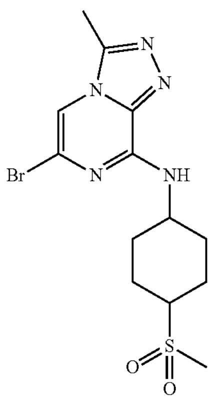 | M + H = 325/327 | VAB |
| K-5 | 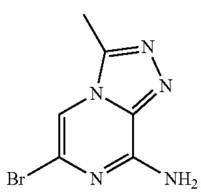 | M + H = 228/230 | VAB |

Preparation of Intermediate L-1

3-methyl-8-[(propan-2-yl)amino]-[1,2,4]triazolo[4,3-a]pyrazine-6-carboxylic acid L-1

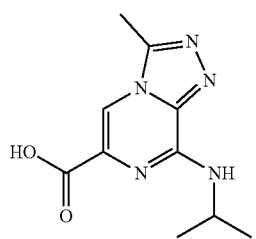 [SMILES: Cc1nnc2c(NC(C)C)nc(C(=O)O)cn12]

6-bromo-3-methyl-N-(propan-2-yl)-[1,2,4]triazolo[4,3-a]pyrazin-8-amine K-1 (10 g; 37.02 mmol), dichloro[1,1'-bis(diphenylphosphino)ferrocene]palladium (II) dichlormethane adduct (3.02 g, 3.70 mmol) and triethylamine (9.35 g; 92.57 mmol) are dissolved in 50 ml methanol and 50 ml NMP. The reaction mixture is stirred for 2 h at 130° C. and 2 bar CO pressure. The reaction mixture is diluted with water and extracted with EtOAc. The organic layer is separated and dried over MgSO₄ and evaporated to dryness. The crude product is purified using method prep. HPLC1. This intermediate is dissolved in 100 ml THF and is treated with 100 ml of a 1 N aqueous LiOH solution. After 1 h the reaction mixture is diluted with water and extracted with DCM. The organic layer is separated and dried over MgSO₄ and evaporated to dryness.

Yield: 57% (5 g; 21.27 mmol)

HPLC-MS: (M+H)+=236; $t_{Ret}$=0.0 min; method VAB

According to the procedures of L-1 the intermediates L-2-L-5 are synthesized.

| # | Structure | MS (M + H)+; $t_{Ret.}$ HPLC [min] | HPLC-Method |
|---|---|---|---|
| L-1 | 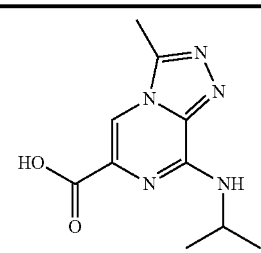 | M + H = 236; $t_{Ret.}$ = 0.0 | VAB |
| L-2 | 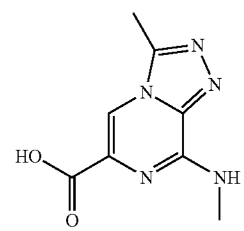 | M + H = 208; $t_{Ret.}$ = 0.0 | VAB |
| L-3 | 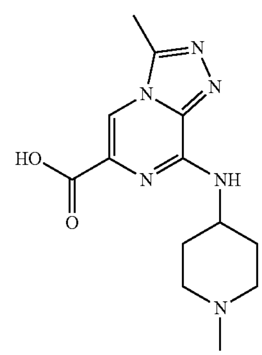 [SMILES: Cc1nnc2c(NC3CCN(C)CC3)nc(C(=O)O)cn12] | M + H = 291; $t_{Ret.}$ = 0.0 | VAB |
| L-4 | 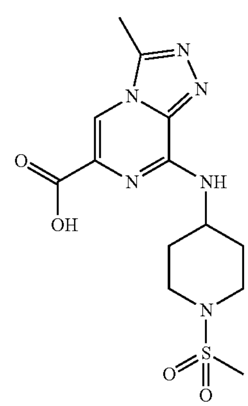 [SMILES: Cc1nnc2c(NC3CCN(S(C)(=O)=O)CC3)nc(C(=O)O)cn12] | M + H = 355; $t_{Ret.}$ = 0.0 | VAB |

| # | Structure | MS (M + H)+; $t_{Ret.}$ HPLC [min] | HPLC-Method |
|---|---|---|---|
| L-5 | 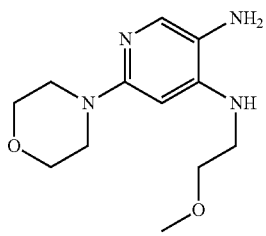 | M + H = 194; $t_{Ret.}$ = 0.0 | VABB5 |

Preparation of Intermediate M-1

4-N-(2-methoxyethyl)-6-(morpholin-4-yl)pyridine-3,4-diamine M-1

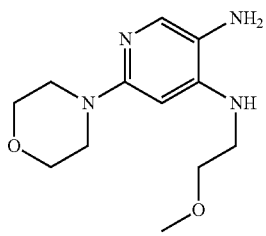 [SMILES: COCCNc1cc(N2CCOCC2)ncc1N]

2,4-Dichloro-5-nitro-pyridine (500 mg; 2.46 mmol), 2-methoxyethylamine (225 nl; 2.46 mmol) and triethylamine (400 µl; 2.82 mmol) are suspended in 2.5 ml NMP and stirred for 1 h at 25° C. To this suspension morpholine (500 µl; 5.71 mmol) is added and the resulting mixture is stirred for 16 h at 50° C. The crude intermediate is purified using reversed phase chromatography (prep. HPLC1). This intermediate is dissolved in 30 ml THF and palladium on carbon is added. The reaction mixture is stirred for 3 h at 25° C. and 4 bar hydrogen pressure. The solid material is filtered off and the solvent is evaporated.

Yield: 70% (430 mg; 1.71 mmol)
HPLC-MS: (M+H)+=253; $t_{Ret}$=1.26 min; method VAB Preparation of Intermediate M-11

5-amino-6-{[(2S)-1-methoxypropan-2-yl]amino}-1,3,3-trimethyl-2,3-dihydro-1H-indol-2-one M-11

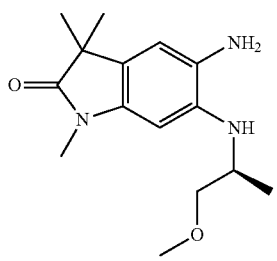 [SMILES: COC[C@H](C)Nc1cc2c(cc1N)C(C)(C)C(=O)N2C]

To a solution of 6-Chloro-5-nitro-1,3-dihydro-indol-2-one (250 mg; 1.18 mmol) in THF super dry (6.000 ml) sodiumhydride (188 mg; 4.70 mmol) is added at 0° C. Then iodomethan (261 µl; 4.12 mmol) is added at 0° C. and the RM is stirred at 25° C. for 18 h. The reaction mixture is poured on water and extracted twice with DCM. The organic phase is dried over MgSO4 and concentrated under reduced pressure. The resulting residue is purified via normal phase chromatography (Column: Interchim IR50-SI 40 g; Flow: 40 ml/min; mobile phase: cyclohexan/ethylacetate=1:1).

This intermediate (200 mg; 0.79 mmol) and (S)-2-Methoxy-1-methyl-ethylamine (425 mg; 4.76 mmol) are dissolved in 1 ml NMP and stirred for 18 h at 80° C. The crude intermediate is purified using reversed phase chromatography (prep. HPLC1). This intermediate is dissolved in 30 ml THF and palladium on carbon is added. The reaction mixture is stirred for 3 h at 25° C. and 4 bar hydrogen pressure.

The solid material is filtered off and the solvent is evaporated.

Yield: 48% (155 mg; 0.56 mmol)
HPLC-MS: (M+H)+=278; $t_{Ret}$=0.70 min; method VAB Preparation of Intermediate M-16

5-amino-6-{[(2S)-1-methoxypropan-2-yl]amino}-3,3-dimethyl-1-(propan-2-yl)-1,3-dihydro-2$\lambda^6$,1-benzothiazole-2,2-dione M-16

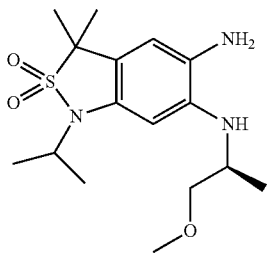 [SMILES: COC[C@H](C)Nc1cc2c(cc1N)C(C)(C)S(=O)(=O)N2C(C)C]

To a solution of 6-chloro-1,3-dihydro-2$\lambda^6$,1-benzothiazole-2,2-dione (400 mg; 1.96 mmol) in 8 ml DMF potassium carbonate (407 mg; 2.95 mmol) is added at 20° C. Then iodopropane (295 µl; 2.95 mmol) is added at 20° C. and the reaction mixture is stirred at 50° C. for 3 h. The reaction mixture is poured on water and extracted twice with DCM. The organic phase is dried over MgSO4 and concentrated under reduced pressure. The crude intermediate is purified using reversed phase chromatography (prep. HPLC1).

This intermediate (370 mg; 1.51 mmol) is dissolved in 10 ml DMSO and sodium hydroxide (1.11 g; 27.9 mmol) is added at 20° C. Then iodomethan (426 µl; 6.78 mmol) is added at 20° C. and the RM is stirred at 20° C. for 2 h. The reaction mixture is poured on water and extracted twice with DCM. The organic phase is dried over MgSO4 and concentrated under reduced pressure. The crude intermediate is purified using reversed phase chromatography (prep. HPLC1).

This intermediate (100 mg; 0.37 mmol) is dissolved in 2 ml acetic acid and fuming nitric acid (23 µl; 0.55 mmol) and 400 µl sulfuric acid are added at 20° C. The reaction mixture is stirred at 20° C. for 3 h. The reaction mixture is poured on water and extracted twice with DCM. The organic phase is dried over MgSO4 and concentrated under reduced pressure.

This intermediate (100 mg; 0.31 mmol) and (S)-2-Methoxy-1-methyl-ethylamine (84 mg; 0.94 mmol) are dissolved in 1 ml NMP and stirred for 18 h at 80° C. The crude intermediate is purified using reversed phase chromatography (prep. HPLC1). This intermediate is dissolved in 30 ml THF and RaNi is added. The reaction mixture is stirred for 3 h at 25° C. and 4 bar hydrogen pressure. The solid material is filtered off and the solvent is evaporated.

Yield: 81 mg; 0.19 mmol
HPLC-MS: $(M+H)^+=342$; $t_{Ret}=0.86$ min; method VAB

Preparation of Intermediate M-17

N1-[(2S)-1-methoxypropan-2-yl]-5-(4-methylmorpholin-2-yl)benzene-1,2-diamine M-17

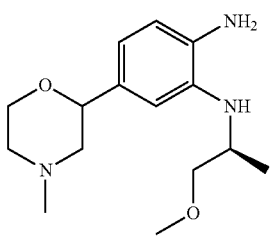 [SMILES: COC[C@H](C)Nc1cc(C2CN(C)CCO2)ccc1N]

To a stirred solution of 3-fluoro-4-nitrobenzoic acid (200 g, 1.08 mol) in THF (2000 mL) is added CDI (210 g, 1.29 mol) portion wise at room temperature. The resulting reaction mixture is stirred at room temperature for 6 h, after that meldrum's acid (155 g, 1.08 mol) is added at room temperature and the resulted reaction mixture is stirred at meldrum's acid for 16 h. The reaction mixture is diluted with 10% HCl solution at 5-10° C. temperature and is stirred for 24 h. The reaction mixture is extracted with ethyl acetate (2×2000 mL), washed with saturated sodium bicarbonate solution and brine, dried over anhydrous sodium sulfate and evaporated under reduced pressure. The crude intermediate is adsorbed on 100-200 silica gel, purified with 20% ethyl acetate/petrol ether. All the pure fractions are collected, evaporated under reduced pressure to afford the intermediate (95 g).

Bromine (68 ml, 0.133 mol) is dissolved in acetic acid (125 mL) and is added drop wise to a stirred solution of the above mentioned intermediate (25 g, 0.136 mol) in acetic acid (125 ml) at room temperature. The resulting reaction mixture is heated at 40° C. for 2 h. The reaction mixture is evaporated under reduced pressure and is diluted with ethyl acetate (500 mL) and water (200 mL). The organic layer was washed with brine, dried over anhydrous sodium sulfate and evaporated under reduced pressure.

This crude intermediate is adsorbed on 230-400 silica gel, purified with 3% ethyl acetate/petrol ether. All the pure fractions are collected evaporated under reduced pressure to afford the intermediate (15 g).

This intermediate (2 g, 7.63 mmol) is dissolved in dichloromethane (20 ml) and N-methyl-ethanolamine (600 μl; 7.63 mmol) and DIPEA (1.4 ml; 8 mmol) are added at room temperature. The resulting reaction mixture is stirred at room temperature for 4 h. The reaction mixture was diluted with DCM (150 mL) and water (50 mL) and the organic layer is separated, washed with brine, dried over anhydride sodium sulfate and evaporated under reduced pressure to afford the crude intermediate.

To stirred solution of this crude intermediate in TFA (20 mL) is added triethyl silane (8 mL) at room temperature. The resulting reaction mixture was refluxed for 16 h. The reaction mixture was diluted with ethyl acetate (250 mL) and water (100 mL), basified with saturated NaHCO3 solution and the organic layer is separated, washed with brine, dried over anhydride sodium sulfate and evaporated under reduced pressure. The crude intermediate was adsorbed on 230-400 silica gel, purified with 1% methanol/dichloromethane. All the pure fractions were collected evaporated under reduced pressure to afford 1.4 g of the intermediate.

This intermediate (200 mg; 0.83 mmol) and (S)-2-Methoxy-1-methyl-ethylamine (168 mg; 1.88 mmol) are dissolved in 2 ml NMP and stirred for 18 h at 80° C. The crude intermediate is purified using reversed phase chromatography (prep. HPLC1).

This intermediate is dissolved in 30 ml THF and RaNi is added. The reaction mixture is stirred for 3 h at 25° C. and 4 bar hydrogen pressure. The solid material is filtered off and the solvent is evaporated.

Yield: 90 mg; 0.32 mmol
HPLC-MS: $(M+H)^+=280$; $t_{Ret}=0.67$ min; method VAB

Preparation of Intermediate M-21

N3-(2-methoxyethyl)-6-(morpholin-4-yl)pyridine-2,3-diamine M-21

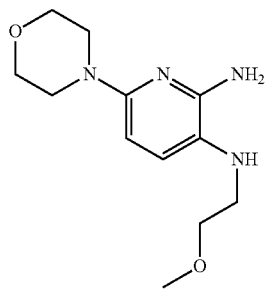 [SMILES: COCCNc1ccc(N2CCOCC2)nc1N]

2-Amino-6-chloro-nitropyridine (250 mg; 1.4 mmol) is added to morpholine (577 μl; 6.6 mmol) and diluted with N,N-dimethylformamid (2 ml). Reaction mixture is stirred at 20° C. for 1 hour. Water is added and the precipitate is collected and suspended in methanol. Solvent is evaporated under reduced pressure.

This intermediate (240 mg; 1.07 mmol) is suspended in 2.4 ml dioxan and di-tert-butyl dicarbonate (596 mg; 2.68 mmol) and DMAP are added. The reaction mixture is stirred at 50° C. for 1 h and then treated with saturated NaHCO3-solution and extracted with DCM. Combined organic phases are dried and concentrated under reduced pressure.

This intermediate is dissolved in 30 ml THF and RaNi is added. The reaction mixture is stirred for 3 h at 25° C. and 4 bar hydrogen pressure. The solid material is filtered off and the solvent is evaporated.

This intermediate (2.00 g; 5.07 mmol) is dissolved in N,N-dimethylformamide (5 ml) followed by addition of potassium carbonate (1.37 g; 10.14 mmol) and 2-bromoethyl methyl ether (1.06 g; 7.60 mmol). After addition is completed the reaction is stirred at 80° C. for 16 h. The solvent is distilled off under reduced pressure and the remaining viscous mass was diluted with water (50 ml). The aqueous layer was extracted with ethyl acetate (3×50 ml) and dried over sodium sulfate and the solvent is removed under reduced pressure. The crude material purified by reverse phase preparative HPLC, give 420 mg of the desired intermediate.

This intermediate is dissolved in HCl in dioxane (4M, 1 ml) and is stirred for 5 h at 20° C. The solvent is evaporated, the crude product is suspended in water and afterwards freeze dried.

Yield: 210 mg; 0.83 mmol

HPLC-MS: (M+H)⁺=253; $t_{Ret}$=0.83 min; method VAB

According to the procedures of M-1, M-11, M-16, M-17 and M-21 the intermediates M-1-M-21 are synthesized.

| # | Structure | MS (M + H)⁺; $t_{Ret.}$ HPLC [min] | HPLC-Method |
|---|---|---|---|
| M-1 | | M + H = 253; $t_{Ret.}$ = 1.26 | FECB5 |
| M-2 | | M + H = 267; $t_{Ret.}$ = 0.62 | VAB |
| M-3 | | M + H = 267; $t_{Ret.}$ = 0.62 | VAB |
| M-4 | | M + H = 281; $t_{Ret.}$ = 1.34 | FSUN2 |
| M-5 | | M + H = 267; $t_{Ret.}$ = 1.35 | FECB5 |
| M-6 | 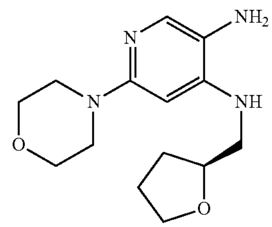 [SMILES: Nc1cnc(N2CCOCC2)cc1NC[C@@H]1CCCO1] | M + H = 279; $t_{Ret.}$ = 0.62 | VAB |
| M-7 | 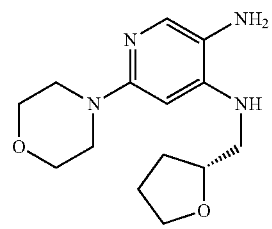 [SMILES: Nc1cnc(N2CCOCC2)cc1NC[C@H]1CCCO1] | M + H = 279; $t_{Ret.}$ = 0.62 | VAB |
| M-8 | 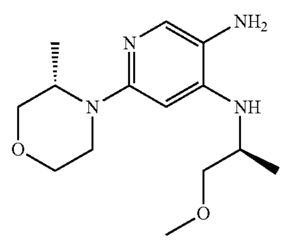 [SMILES: COC[C@H](C)Nc1cc(N2CCOC[C@@H]2C)ncc1N] | M + H = 281; $t_{Ret.}$ = 0.69 | VAB |
| M-9 | 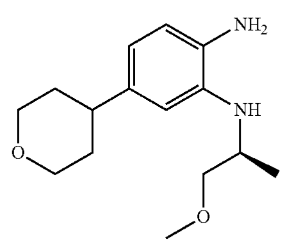 [SMILES: COC[C@H](C)Nc1cc(C2CCOCC2)ccc1N] | M + H = 264; $t_{Ret.}$ = 0.77 | VAB |
| M-10 | 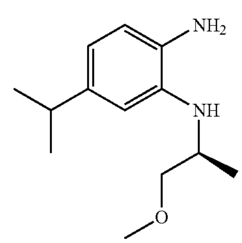 [SMILES: COC[C@H](C)Nc1cc(C(C)C)ccc1N] | M + H = 223; $t_{Ret.}$ = 0.92 | FECB5 |
| M-11 | 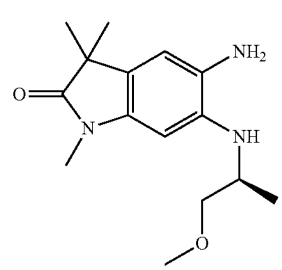 [SMILES: COC[C@H](C)Nc1cc2c(cc1N)C(C)(C)C(=O)N2C] | M + H = 278; $t_{Ret.}$ = 0.70 | VAB |

| # | Structure | MS (M + H)+; t_Ret. HPLC [min] | HPLC-Method |
|---|---|---|---|
| M-12 | 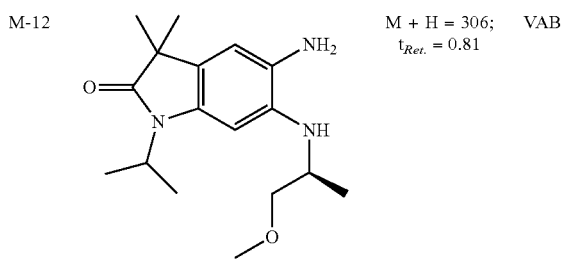 | M + H = 306; $t_{Ret.}$ = 0.81 | VAB |
| M-13 | 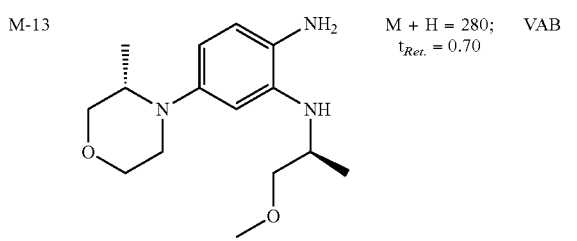 | M + H = 280; $t_{Ret.}$ = 0.70 | VAB |
| M-14 | 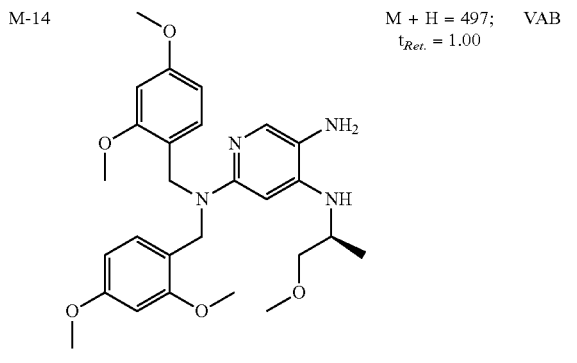 | M + H = 497; $t_{Ret.}$ = 1.00 | VAB |
| M-15 | 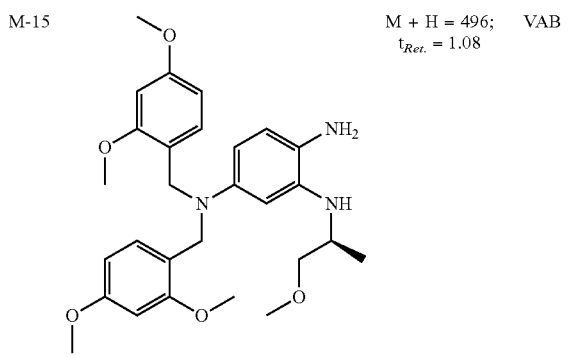 | M + H = 496; $t_{Ret.}$ = 1.08 | VAB |
| M-16 | 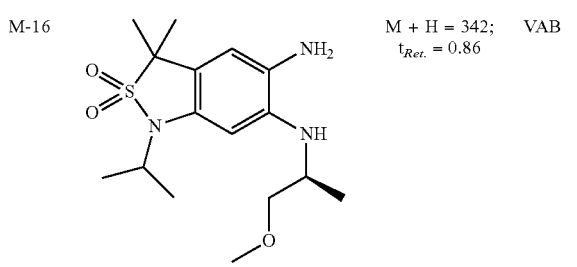 | M + H = 342; $t_{Ret.}$ = 0.86 | VAB |
| # | Structure | MS (M + H)+; t_Ret. HPLC [min] | HPLC-Method |
|---|---|---|---|
| M-17 | 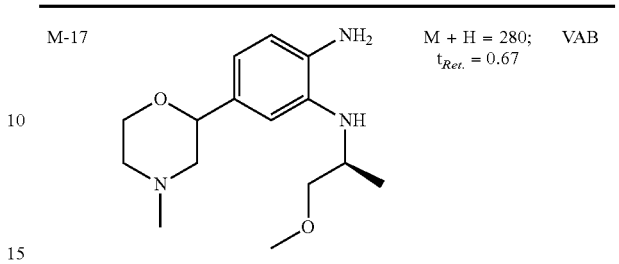 | M + H = 280; $t_{Ret.}$ = 0.67 | VAB |
| M-18 | 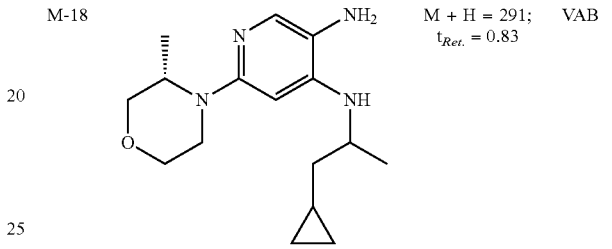 | M + H = 291; $t_{Ret.}$ = 0.83 | VAB |
| M-19 | 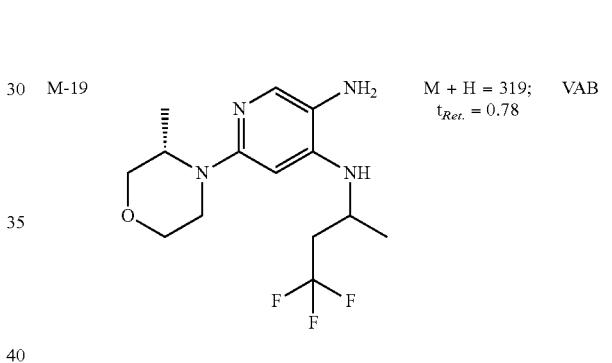 | M + H = 319; $t_{Ret.}$ = 0.78 | VAB |
| M-20 | 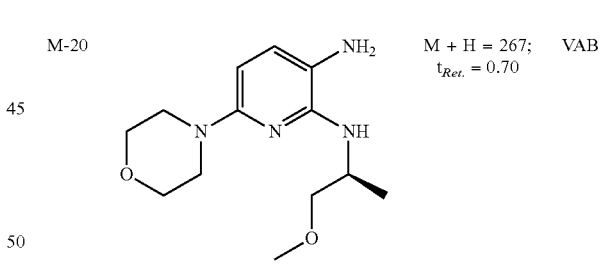 | M + H = 267; $t_{Ret.}$ = 0.70 | VAB |
| M-21 | 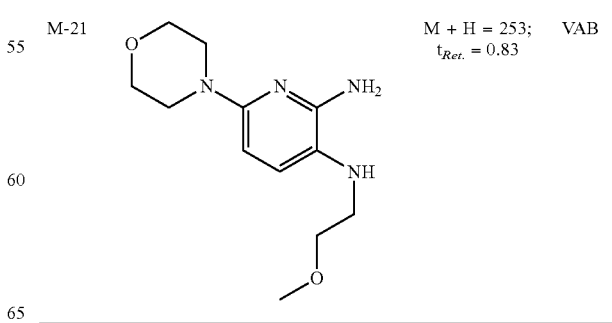 | M + H = 253; $t_{Ret.}$ = 0.83 | VAB |

General Method for Preparation of Compounds of Formula I

6-[1-(2-methoxyethyl)-6-(morpholin-4-yl)-1H-imidazo[4,5-c]pyridin-2-yl]-3-methyl-N-(propan-2-yl)-[1,2,4]triazolo[4,3-a]pyrazin-8-amine I-1

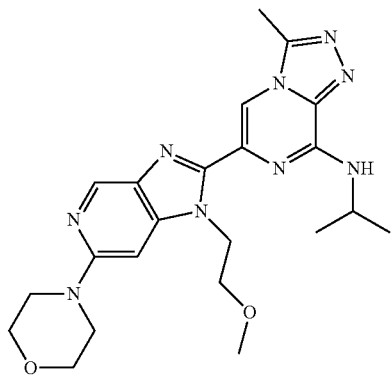 [SMILES: COCCn1c(-c2cn3c(C)nnc3c(NC(C)C)n2)nc2cnc(N3CCOCC3)cc21]

3-methyl-8-[(propan-2-yl)amino]-[1,2,4]triazolo[4,3-a]pyrazine-6-carboxylic acid L-1 (58 mg; 0.25 mmol), Hünig-base (125 µl; 0.77 mmol) and HATU (100 mg; 0.26 mmol) are dissolved in 2 ml NMP. The reaction mixture is stirred for 10 min, then 4-N-(2-methoxyethyl)-6-(morpholin-4-yl)pyridine-3,4-diamine M-1 (63 mg; 0.25 mmol) is added and the resulting mixture is stirred for an additional 5 h at 25° C. The reaction mixture is diluted with water and DCM. The organic layer is separated and dried over MgSO₄ and the solvent is evaporated. The crude intermediate is dissolved in 4 ml acetic acid and stirred at 160° C. for 2 h.

Afterwards the reaction mixture is neutralized with aqueous NaHCO₃ solution and extracted with DCM. The organic layer is separated and dried over MgSO₄ and the solvent is evaporated. The crude product is purified using reversed phase chromatography (Method: prep. HPLC1).

Yield: 24% (28 mg; 0.06 mmol)

HPLC-MS: (M+H)⁺=452; $t_{Ret}$=0.93 min; method LCMS-BAS1

According to I-1 the following examples are synthesized. For some examples (e.g. I-18 and I-20) the protection group needs to be cleaved off.

| # | Structure | MS (M + H)⁺; $t_{Ret.}$ HPLC [min] | HPLC-Method |
|---|---|---|---|
| I-1 | 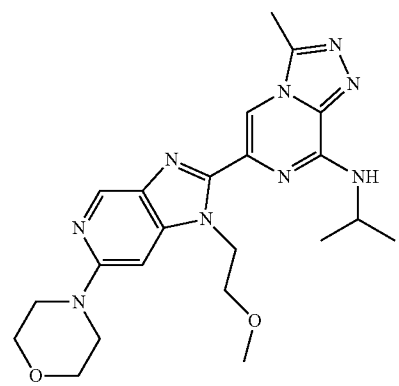 [SMILES: COCCn1c(-c2cn3c(C)nnc3c(NC(C)C)n2)nc2cnc(N3CCOCC3)cc21] | M + H = 452; $t_{Ret.}$ = 0.93 | LCMSBAS1 |
| I-2 | 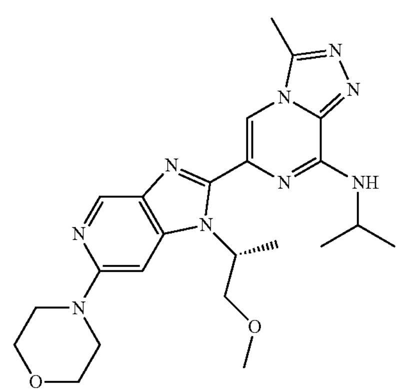 [SMILES: COC[C@@H](C)n1c(-c2cn3c(C)nnc3c(NC(C)C)n2)nc2cnc(N3CCOCC3)cc21] | M + H = 466; $t_{Ret.}$ = 1.02 | LCMSBAS1 |

-continued

| # | Structure | MS (M + H)+; t_Ret. HPLC [min] | HPLC-Method |
|---|---|---|---|
| I-3 | 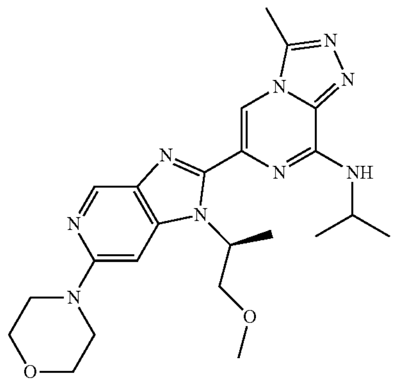 [SMILES: COC[C@H](C)n1c(-c2cn3c(C)nnc3c(NC(C)C)n2)nc2cnc(N3CCOCC3)cc21] | M + H = 466; t_Ret. = 1.02 | LCMSBAS1 |
| I-4 | 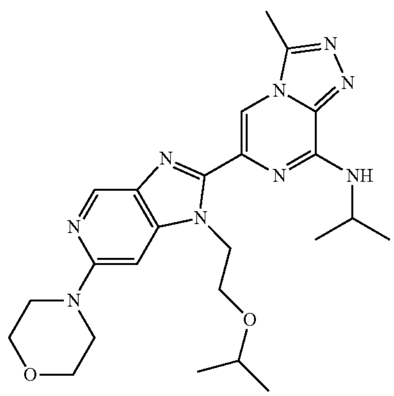 [SMILES: Cc1nnc2c(NC(C)C)nc(-c3nc4cnc(N5CCOCC5)cc4n3CCOC(C)C)cn12] | M + H = 480; t_Ret. = 1.05 | LCMSBAS1 |
| I-5 | 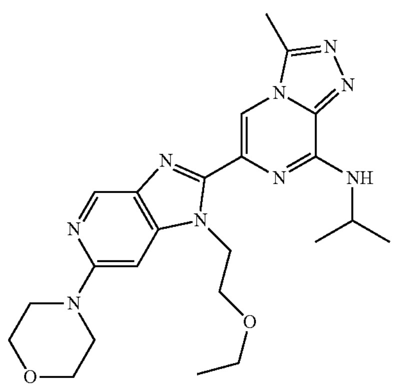 [SMILES: CCOCCn1c(-c2cn3c(C)nnc3c(NC(C)C)n2)nc2cnc(N3CCOCC3)cc21] | M + H = 466; t_Ret. = 0.99 | LCMSBAS1 |
| I-6 | 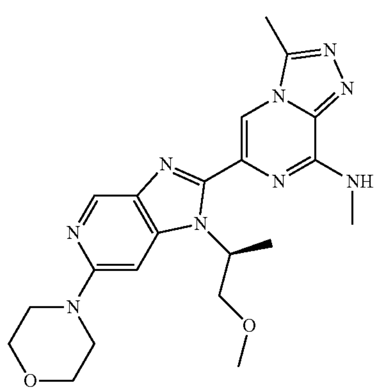 [SMILES: CNc1nc(-c2nc3cnc(N4CCOCC4)cc3n2[C@@H](C)COC)cn2c(C)nnc12] | M + H = 438; t_Ret. = 0.88 | LCMSBAS1 |

-continued

| # | Structure | MS (M + H)+; $t_{Ret.}$ HPLC [min] | HPLC-Method |
|---|---|---|---|
| I-7 | 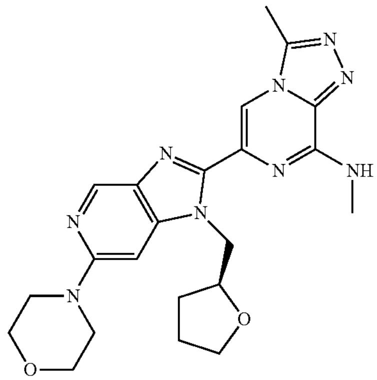 [SMILES: CNc1nc(-c2nc3cnc(N4CCOCC4)cc3n2C[C@@H]2CCCO2)cn2c(C)nnc12] | M + H = 450; $t_{Ret.}$ = 0.88 | LCMSBAS1 |
| I-8 | 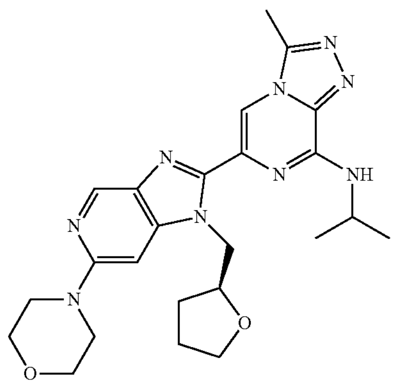 [SMILES: Cc1nnc2c(NC(C)C)nc(-c3nc4cnc(N5CCOCC5)cc4n3C[C@@H]3CCCO3)cn12] | M + H = 478; $t_{Ret.}$ = 1.01 | LCMSBAS1 |
| I-9 | 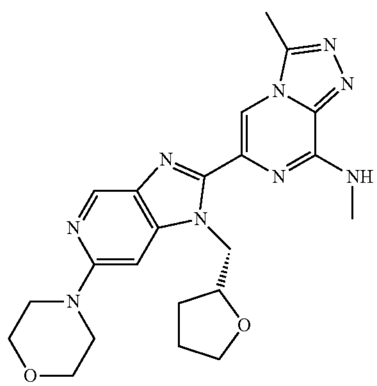 | M + H = 450; $t_{Ret.}$ = 0.88 | LCMSBAS1 |
| I-10 | 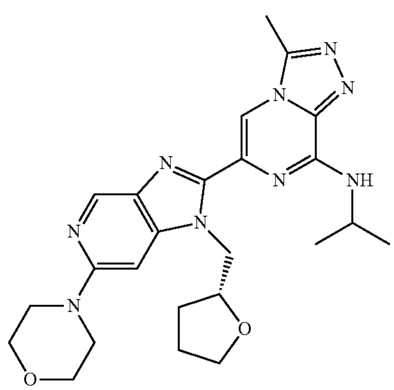 [SMILES: Cc1nnc2c(NC(C)C)nc(-c3nc4cnc(N5CCOCC5)cc4n3C[C@H]3CCCO3)cn12] | M + H = 478; $t_{Ret.}$ = 1.01 | LCMSBAS1 |

-continued

| # | Structure | MS (M + H)+; t_Ret. HPLC [min] | HPLC-Method |
|---|---|---|---|
| I-11 | 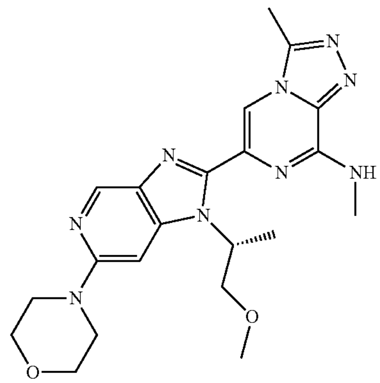 [SMILES: CNc1nc(-c2nc3cnc(N4CCOCC4)cc3n2[C@H](C)COC)cn2c(C)nnc12] | M + H = 438; t_Ret. = 0.88 | LCMSBAS1 |
| I-12 | 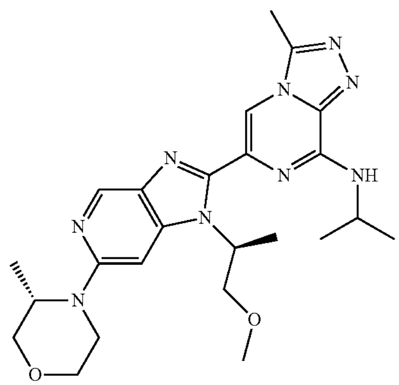 | M + H = 480; t_Ret. = 1.08 | LCMSBAS1 |
| I-13 | 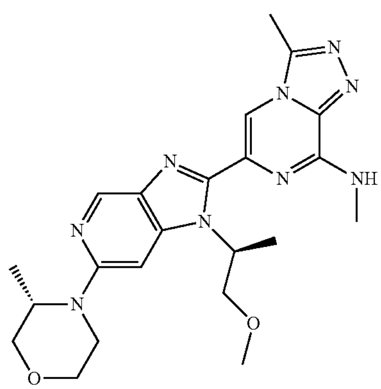 [SMILES: CNc1nc(-c2nc3cnc(N4CCOC[C@@H]4C)cc3n2[C@@H](C)COC)cn2c(C)nnc12] | M + H = 452; t_Ret. = 0.95 | LCMSBAS1 |
| I-14 | 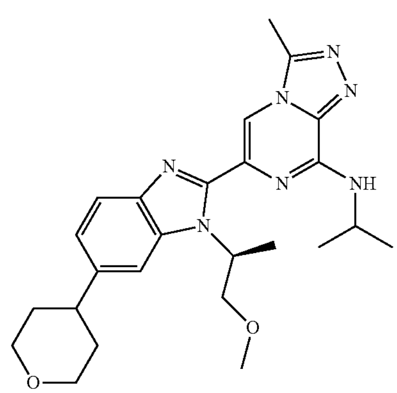 [SMILES: COC[C@H](C)n1c(-c2cn3c(C)nnc3c(NC(C)C)n2)nc2ccc(C3CCOCC3)cc21] | M + H = 464; t_Ret. = 1.17 | LCMSBAS1 |

-continued

| # | Structure | MS (M + H)+; t_Ret. HPLC [min] | HPLC-Method |
|---|---|---|---|
| I-15 | 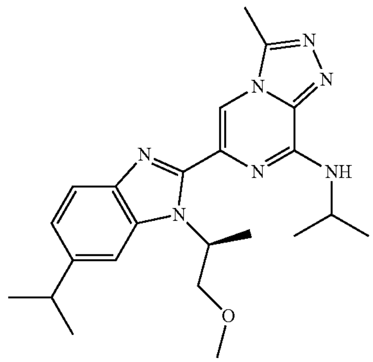 [SMILES: COC[C@H](C)n1c(-c2cn3c(C)nnc3c(NC(C)C)n2)nc2ccc(C(C)C)cc21] | M + H = 422; t_Ret. = 1.36 | LCMSBAS1 |
| I-16 | 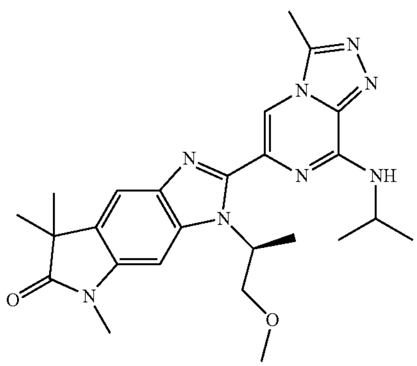 [SMILES: COC[C@H](C)n1c(-c2cn3c(C)nnc3c(NC(C)C)n2)nc2cc3c(cc21)N(C)C(=O)C3(C)C] | M + H = 477; t_Ret. = 1.08 | LCMSBAS1 |
| I-17 | 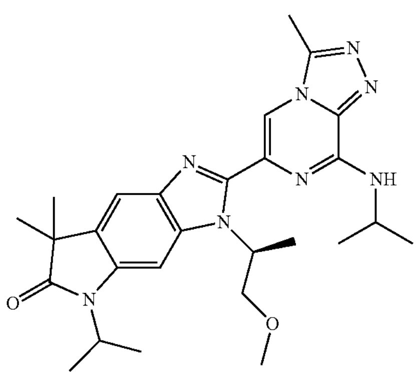 [SMILES: COC[C@H](C)n1c(-c2cn3c(C)nnc3c(NC(C)C)n2)nc2cc3c(cc21)N(C(C)C)C(=O)C3(C)C] | M + H = 523; t_Ret. = 1.22 | LCMSBAS1 |
| I-18 | 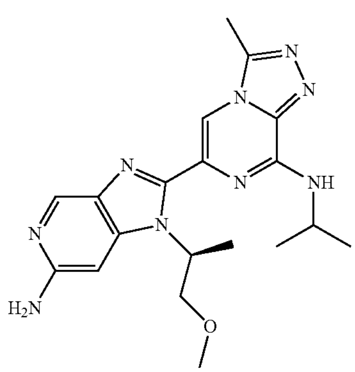 [SMILES: COC[C@H](C)n1c(-c2cn3c(C)nnc3c(NC(C)C)n2)nc2cnc(N)cc21] | M + H = 396; t_Ret. = 0.51 | LCMSBAS1 |

-continued

| # | Structure | MS (M + H)+; t_Ret. HPLC [min] | HPLC-Method |
|---|---|---|---|
| I-19 | 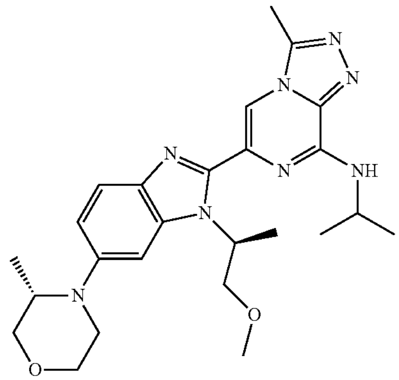 [SMILES: COC[C@H](C)n1c(-c2cn3c(C)nnc3c(NC(C)C)n2)nc2ccc(N3CCOC[C@@H]3C)cc21] | M + H = 479; t_Ret. = 1.28 | LCMSBAS1 |
| I-20 | 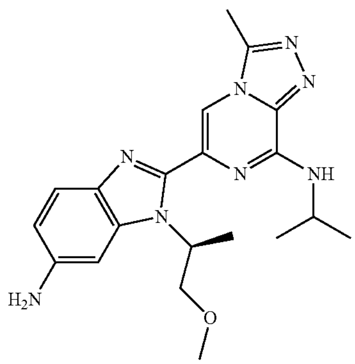 | M + H = 395; t_Ret. = 0.56 | LCMSBAS1 |
| I-21 | 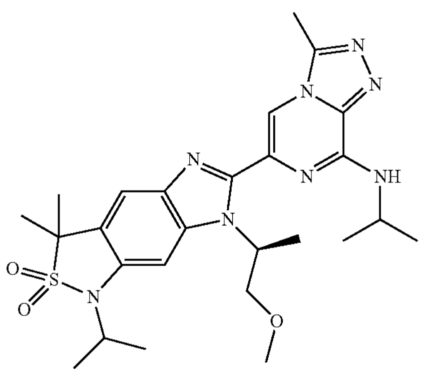 [SMILES: COC[C@H](C)n1c(-c2cn3c(C)nnc3c(NC(C)C)n2)nc2cc3c(cc21)N(C(C)C)S(=O)(=O)C3(C)C] | M + H = 541; t_Ret. = 1.27 | LCMSBAS1 |
| I-22 | 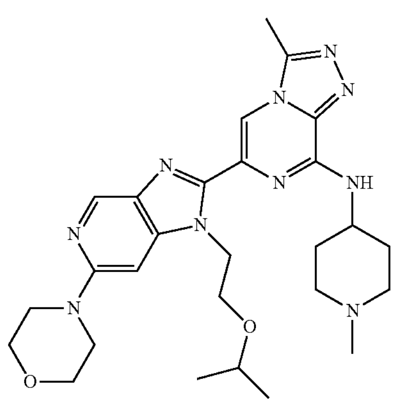 [SMILES: Cc1nnc2c(NC3CCN(C)CC3)nc(-c3nc4cnc(N5CCOCC5)cc4n3CCOC(C)C)cn12] | M + H = 535; t_Ret. = 1.02 | LCMSBAS1 |

-continued

| # | Structure | MS (M + H)+; t_Ret. HPLC [min] | HPLC-Method |
|---|---|---|---|
| I-23 | 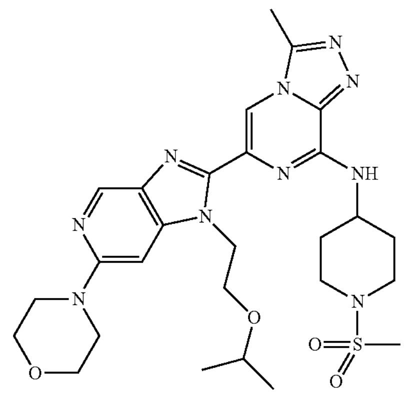 [SMILES: Cc1nnc2c(NC3CCN(S(C)(=O)=O)CC3)nc(-c3nc4cnc(N5CCOCC5)cc4n3CCOC(C)C)cn12] | M + H = 599; t_Ret. = 1.00 | LCMSBAS1 |
| I-24 | 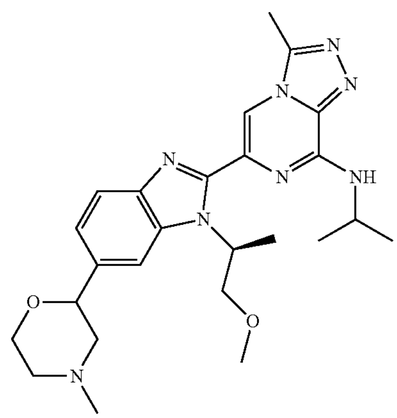 [SMILES: COC[C@H](C)n1c(-c2cn3c(C)nnc3c(NC(C)C)n2)nc2ccc(C3CN(C)CCO3)cc21] | M + H = 479; t_Ret. = 1.05 | LCMSBAS1 |
| I-25 | 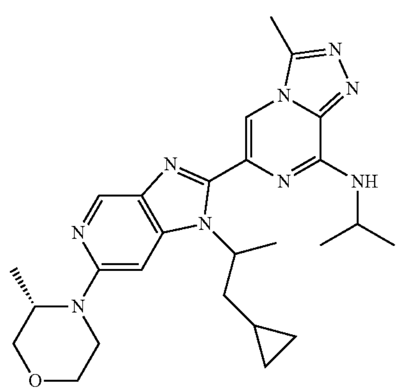 [SMILES: Cc1nnc2c(NC(C)C)nc(-c3nc4cnc(N5CCOC[C@@H]5C)cc4n3C(C)CC3CC3)cn12] | M + H = 490; t_Ret. = 1.22 | LCMSBAS1 |
| I-26 | 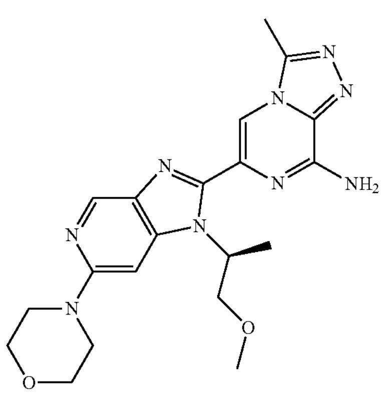 [SMILES: COC[C@H](C)n1c(-c2cn3c(C)nnc3c(N)n2)nc2cnc(N3CCOCC3)cc21] | M + H = 424; t_Ret. = 0.77 | LCMSBAS1 |

-continued

| # | Structure | MS (M + H)⁺; t_Ret. HPLC [min] | HPLC-Method |
|---|---|---|---|
| I-27 | 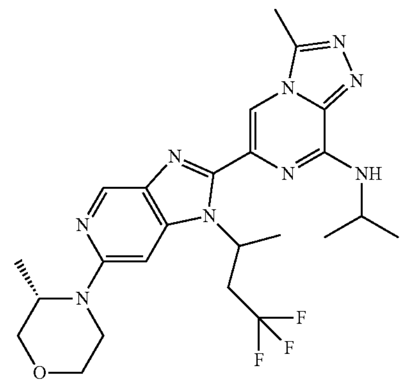 [SMILES: Cc1nnc2c(NC(C)C)nc(-c3nc4cnc(N5CCOC[C@@H]5C)cc4n3C(C)CC(F)(F)F)cn12] | M + H = 518; t_Ret. = 1.14 | LCMSBAS1 |
| I-28 | 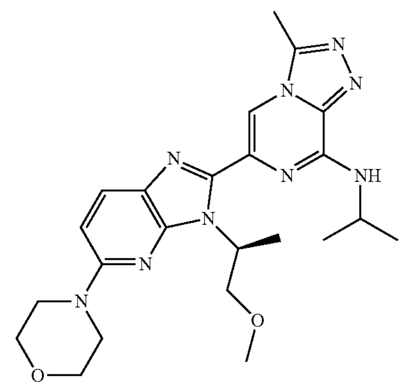 | M + H = 466; t_Ret. = 1.13 | LCMSBAS1 |
| I-29 | 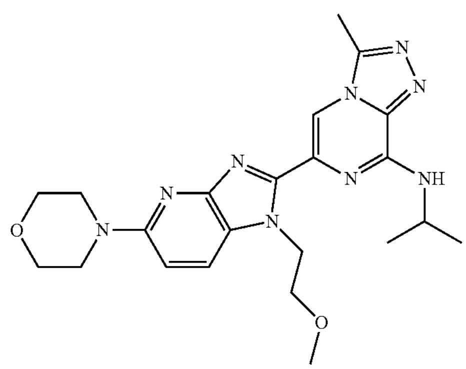 [SMILES: COCCn1c(-c2cn3c(C)nnc3c(NC(C)C)n2)nc2nc(N3CCOCC3)ccc21] | M + H = 452; t_Ret. = 1.01 | LCMSBAS1 |

Biological Methods

BRD4-H4 Tetraacetylated Peptide Inhibition AlphaScreen

This assay is used to determine whether the compounds inhibit the interaction between the first (BRD4-BD1) or the second (BRD4-BD2) bromodomain of BRD4 and the tetraacetylated histone H4 peptide.

Compounds are diluted in serial dilution 1:5 in assay buffer from 10 mM stock in DMSO (100 µM start concentration) in white OptiPlate-384 (PerkinElmer). A mix consisting of 15 nM GST-BRD4-BD1 protein (aa 44-168) or 150 nM GST-BRD4-BD2 (aa 333-460) and 15 nM biotinylated Acetyl-Histone H4 (Lys5, 8, 12, 16) peptide is prepared in assay buffer (50 mM HEPES pH=7.4; 25 mM NaCl; 0.05% Tween 20; 0.1% bovine serum albumin (BSA); 10 mM dithiothreitol (DTT)). 6 µl of the mix is added to the compound dilutions. Subsequently, 6 µl of premixed AlphaLISA Glutathione Acceptor Beads and AlphaScreen Streptavidin Donor Beads from PerkinElmer (in assay buffer at a concentration of 10 µg/ml each) are added and the samples are incubated for 30 min at RT in the dark (shaking 300 rpm). Afterwards, the signal is measured in a PerkinElmer Envision HTS Multilabel Reader using the AlphaScreen protocol from PerkinElmer.

Each plate contains negative controls where biotinylated Acetyl-Histone H4 peptide and GST-BRD4-BD1 or GST-BRD4-BD2 are left out and replaced by assay buffer. Negative control values are entered as low basis value when using the software GraphPad Prism for calculations. Furthermore, a positive control (probe molecule JQ1+ with protein/peptide mix) is pipetted. Determination of $IC_{50}$ values are carried out using GraphPad Prism 3.03 software (or updates thereof).

Table summarizing the $IC_{50}$ of the compounds of the invention exemplified above

| Ex # | BRD4-BD1<br>$IC_{50}$ [nM] |
|---|---|
| I-1 | 32 |
| I-2 | 333 |
| I-3 | 33 |
| I-4 | 43 |
| I-5 | 33 |
| I-6 | 51 |
| I-7 | 55 |
| I-8 | 55 |
| I-9 | 65 |
| I-10 | 54 |
| I-11 | 549 |
| I-12 | 51 |
| I-13 | 27 |
| I-14 | 49 |
| I-15 | 123 |
| I-16 | 22 |
| I-17 | 18 |
| I-18 | 69 |
| I-19 | 58 |
| I-20 | 157 |
| I-21 | 17 |
| I-22 | 35 |
| I-23 | 122 |
| I-24 | 63 |
| I-25 | 9 |
| I-26 | 123 |
| I-27 | 26 |
| I-28 | 69 |
| I-29 | 49 |

On the basis of their biological properties the compounds of general formula (1) according to the invention, their tautomers, racemates, enantiomers, diastereomers, mixtures thereof and the salts of all the above-mentioned forms are suitable for treating diseases characterised by virus infection, inflammatory diseases and abnormal cell proliferation, such as cancer.

For example, the following cancers may be treated with compounds according to the invention, without being restricted thereto: brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon carcinoma, colorectal carcinoma, anal carcinoma, carcinoma of the large bowel, tumours of the small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas (NSCLC) such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma (MM)), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma such as for example vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva.

Preferred cancers, which may be treated with compounds according to the invention, are hematopoietic malignancies (including but not limited to AML, MM), as well as solid tumors including but not limited to lung, liver, colon, brain, thyroid, pancreas, breast, ovary and prostate cancer.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (I) may be used on their own or in combination with other active substances according to the invention, optionally also in combination with other pharmacologically active substances.

Chemotherapeutic agents which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosine kinase inhibitors, such as for example cetuximab, gefitinib, imatinib, lapatinib and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Other possible combination partners are 2-chlorodesoxyadenosine, 2-fluorodesoxycytidine, 2-methoxyoestradiol, 2C4,3-alethine, 131-I-TM-601, 3CPA, 7-ethyl-10-hydroxycamptothecin, 16-aza-epothilone B, A 105972, A 204197, aldesleukin, alitretinoin, altretamine, alvocidib, amonafide, anthrapyrazole, AG-2037, AP-5280, apaziquone, apomine, aranose, arglabin, arzoxifene, atamestane, atrasentan, auristatin PE, AVLB, AZ10992, ABX-EGF, ARRY-300, ARRY-142886/AZD-6244, ARRY-704/AZD-8330, AS-703026, azacytidine, azaepothilone B, azonafide, BAY-43-9006, BBR-3464, BBR-3576, bevacizumab, biricodar dicitrate, BCX-1777, bleocin, BLP-25, BMS-184476, BMS-247550, BMS-188797, BMS-275291, BNP-1350, BNP-7787, BIBW 2992 (afatinib), BIBF 1120 (Vargatef™), bleomycinic acid, bleomycin A, bleomycin B, bryostatin-1, bortezomib, brostallicin, busulphan, CA-4 prodrug, CA-4, CapCell, calcitriol, canertinib, canfosfamide, capecitabine, carboxyphthalatoplatin, CCI-779, CEP-701, CEP-751, CBT-1 cefixime, ceflatonin, ceftriaxone, celecoxib, celmoleukin, cemadotin, CH4987655/RO-4987655, chlorotrianisene, cilengitide, ciclosporin, CDA-II, CDC-394, CKD-602, clofarabin, colchicin, combretastatin A4, CHS-828, CLL-Thera, CMT-3 cryptophycin 52, CTP-37, CP-461, CV-247, cyanomorpholinodoxorubicin, cytarabine, D 24851, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, E7010, E-6201, edatrexat, edotreotide, efaproxiral, eflornithine, EKB-569, EKB-509, elsamitrucin, epothilone B, epratuzumab, ER-86526, erlotinib, ET-18-OCH3, ethynylcytidine, ethynyloestradiol, exatecan, exatecan mesylate, exemestane, exisulind, fenretinide, floxuridine, folic acid, FOLFOX, FOLFIRI, formestane, galarubicin, gallium maltolate, gefinitib, gemtuzumab, gimatecan, glufosfamide, GCS-IOO, G17DT immunogen, GMK, GPX-100, GSK-5126766, GSK-1120212, GW2016, granisetron, hexamethylmelamine, histamine, homoharringtonine, hyaluronic acid, hydroxyurea, hydroxyprogesterone caproate, ibandronate, ibritumomab, idatrexate, idenestrol, IDN-5109, IMC-1C11, immunol, indisulam, interferon alpha-2a, interferon alfa-2b, interleukin-2, ionafarnib, iproplatin, irofulven, isohomohalichondrin-B, isoflavone, isotretinoin, ixabepilone, JRX-2, JSF-154, J-107088, conjugated oestrogens, kahalid F, ketoconazole, KW-2170, lobaplatin, leflunomide, lenograstim, leuprolide, leuporelin, lexidronam, LGD-1550, linezolid, lutetium texaphyrin, lometrexol, losoxantrone, LU 223651, lurtotecan, mafosfamide, marimastat, mechloroethamine, methyltestosteron, methylprednisolone, MEN-10755, MDX-H210, MDX-447, MGV, midostaurin, minodronic acid, mitomycin, mivobulin, MK-2206, MLN518, motexafin gadolinium, MS-209, MS-275, MX6, neridronate, neovastat, nimesulide, nitroglycerin, nolatrexed, norelin, N-acetylcysteine, 06-benzylguanine, omeprazole, oncophage, ormiplatin, ortataxel, oxantrazole, oestrogen, patupilone, pegfilgrastim, PCK-3145, pegfilgrastim, PBI-1402, PEG-paclitaxel, PEP-005, P-04, PKC412, P54, PI-88, pelitinib, pemetrexed, pentrix, perifosine, perillylalcohol, PG-TXL, PG2, PLX-4032/RO-5185426, PT-100, picoplatin, pivaloyloxymethylbutyrate, pixantrone, phenoxodiol O, PKI166, plevitrexed, plicamycin, polyprenic acid, porfiromycin, prednisone, prednisolone, quinamed, quinupristin, RAF-265, ramosetron, ranpirnase, RDEA-119/BAY 869766, rebeccamycin analogues, revimid, RG-7167, rhizoxin, rhu-MAb, risedronate, rituximab, rofecoxib, Ro-31-7453, RO-5126766, RPR 109881A, rubidazon, rubitecan, R-flurbiprofen, S-9788, sabarubicin, SAHA, sargramostim, satraplatin, SB 408075, SU5416, SU6668, SDX-101, semustin, seocalcitol, SM-11355, SN-38, SN-4071, SR-27897, SR-31747, SRL-172, sorafenib, spiroplatin, squalamine, suberanilohydroxamic acid, sutent, T 900607, T 138067, TAS-103, tacedinaline, talaporfin, tariquitar, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymectacin, tiazofurin, tipifarnib, tirapazamine, tocladesine, tomudex, toremofin, trabectedin, TransMID-107, transretinic acid, traszutumab, tretinoin, triacetyluridine, triapine, trimetrexate, TLK-286TXD 258, urocidin, valrubicin, vatalanib, vincristine, vinflunine, virulizin, WX-UK1, vectibix, Volasertib (or other polo-like kinae inhibitors), xeloda, XELOX, XL-281, XL-518/R-7420, YM-511, YM-598, ZD-4190, ZD-6474, ZD-4054, ZD-0473, ZD-6126, ZD-9331, ZDI839, zoledronat and zosuquidar.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavouring enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

| A) | |
|---|---|
| Tablets | per tablet |
| active substance according to formula (I) | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | |
|---|---|
| Tablets | per tablet |
| active substance according to formula (I) | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) | |
|---|---|
| Ampoule solution | |
| active substance according to formula (I) | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:

1. A compound of formula (I)

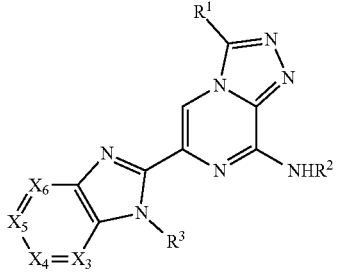

wherein,
R$^1$ is —C$_{1-3}$alkyl or —C$_{1-3}$haloalkyl;
R$^2$ is hydrogen or —C$_{1-3}$alkyl, or
R$^2$ is 4-7 membered heterocycloalkyl, wherein the heterocycloalkyl group can be optionally and independently substituted with one or more groups independently selected from the group consisting of —C$_{1-3}$alkyl, —C(O)(C$_{1-3}$alkyl)$_2$ and —S(O)$_2$(C$_{1-3}$alkyl)$_2$;
R$^3$ is —C$_{1-4}$alkyl substituted with one or more groups independently selected from the group consisting of halogen, —C$_{1-2}$haloalkyl, —O—C$_{1-3}$alkyl, —O—C$_{1-3}$halolkyl, 4-7 membered heterocycloalkyl, and —C$_{3-7}$ cycloalkyl;
X$_3$ is —CH= or —N=;
X$_4$ is —CR$^4$= or —N=;
X$_5$ is —CR$^5$= or —N=;
X$_6$ is —CH= or —N=;
wherein none, one or two X$_3$ to X$_6$ can be —N=;
R$^4$ is selected from the group consisting of hydrogen, halogen, —CN, —NH$_2$, —O—C$_{1-3}$alkyl, —N(C$_{1-3}$alkyl)$_2$, —C(O)N(C$_{1-3}$alkyl)$_2$ and —C$_{1-5}$alkyl, wherein the —C$_{1-5}$alkyl group can be optionally and independently substituted with one or more groups independently selected from the group consisting of halogen and —CN, or
R$^4$ is 4-7 membered heterocycloalkyl, wherein the heterocycloalkyl group can be optionally and independently substituted with one or more —C$_{1-3}$alkyl, or
R$^4$ is a —C$_{3-6}$cycloalkyl wherein the cycloalkyl group can be optionally and independently substituted with one or more groups independently selected from the group consisting of C$_{1-3}$alkyl, —C$_{1-3}$haloalkyl and halogen;
R$^5$ is hydrogen, halogen, or —N(C$_{1-3}$alkyl)$_2$, or
R$^5$ is 4-7 membered heterocycloalkyl, wherein the heterocycloalkyl group is optionally and independently substituted with one or more —C$_{1-3}$alkyl;
wherein R$^4$ and R$^5$ cannot be both hydrogen;
or when X$_4$ is —CR$^4$ and X$_5$ is —CR$^5$, R$^4$ and R$^5$ together can form 5 membered heterocycloalkyl selected from the group consisting of

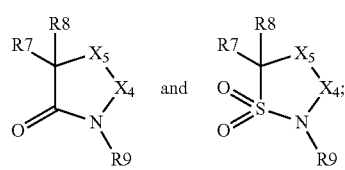

R$^7$ is —C$_{1-3}$alkyl or —C$_{1-3}$haloalkyl;
R$^8$ is —C$_{1-3}$alkyl or —C$_{1-3}$haloalkyl;
R$^9$ is —C$_{1-3}$alkyl or —C$_{1-3}$haloalkyl;
or a salt thereof.

2. A compound according to claim 1 of formula (Ia),

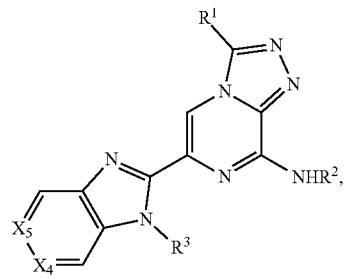

wherein R$^1$, R$^2$, R$^3$, X$_4$ and X$_5$ are as defined in claim 1.

3. A compound according to claim 1, wherein R$^2$ is hydrogen, isopropyl, methyl or piperidine, wherein the piperidine is N-substituted with methyl or —SO$_2$CH$_3$.

4. A compound according to claim 1, wherein R$^2$ is isopropyl or methyl.

5. A compound according to claim 1, wherein R$^3$ is —C$_{1-4}$alkyl substituted with one —O—C$_{1-3}$alkyl, —C$_{1-2}$haloalkyl, —C$_{3-7}$ cycloalkyl or 5 membered heterocycloalkyl.

6. A compound according to claim 5, wherein R$^3$ is —(CH$_2$)$_2$—O—CH$_3$, —CH(CH$_3$)—CH$_2$—O—CH$_3$, —(CH$_2$)$_2$—O—CH(CH$_3$)$_2$, —(CH$_2$)$_2$—O—CH$_2$—CH$_3$, —CH$_2$-tetrahydrofuran, —CH(CH$_3$)—CH$_2$-cyclopropyl or —CH(CH$_3$)—CH$_2$—CF$_3$.

7. A compound according to claim 1, wherein R$^4$ is selected from the group consisting of hydrogen, —C$_{1-3}$alkyl, NH$_2$, and 6 membered heterocycloalkyl, which heterocycloalkyl is optionally substituted by one methyl.

8. A compound according to claim 7, wherein R$^4$ is selected from the group consisting of hydrogen, —CH(CH$_3$)$_2$, NH$_2$, tetrahydropyran and morpholine, which morpholine is optionally substituted with one methyl.

9. A compound according to claim 1, wherein R$^5$ is hydrogen or morpholine.

10. A compound according to claim 1, wherein X$_4$ is —CR$^4$= and X$_5$ is —CR$^5$=, R$^4$ and R$^5$ are taken together to form

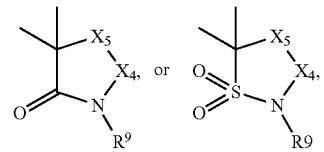

wherein R$^9$ is —C$_{1-3}$alkyl.

11. A compound according to claim 10, wherein X$_4$ is —CR$^4$= and X$_5$ is —CR$^5$=, R$^4$ and R$^5$ are taken together to form

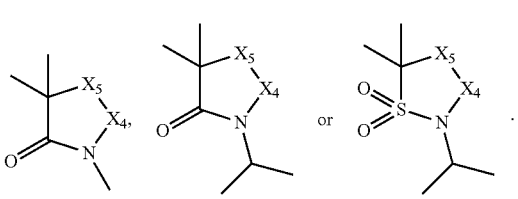

12. A compound according to claim 1, wherein X$_5$ is —N=.

13. A compound according to claim 1, wherein X$_5$ is —CH=.

14. A compound according to claim 1 selected from the group consisting of:

| # | Structure | # | Structure |
|---|---|---|---|
| I-1 | 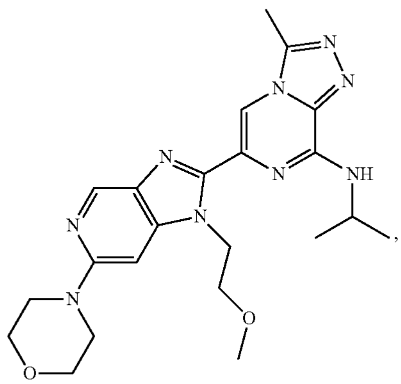 [SMILES: COCCn1c(-c2cn3c(C)nnc3c(NC(C)C)n2)nc2cnc(N3CCOCC3)cc21] | I-2 | 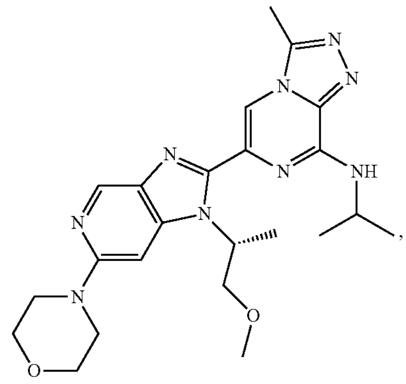 [SMILES: COC[C@@H](C)n1c(-c2cn3c(C)nnc3c(NC(C)C)n2)nc2cnc(N3CCOCC3)cc21] |
| I-3 | 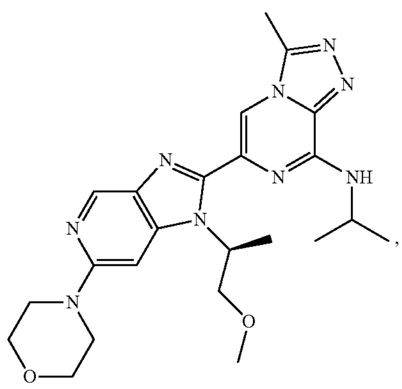 [SMILES: COC[C@H](C)n1c(-c2cn3c(C)nnc3c(NC(C)C)n2)nc2cnc(N3CCOCC3)cc21] | I-4 | 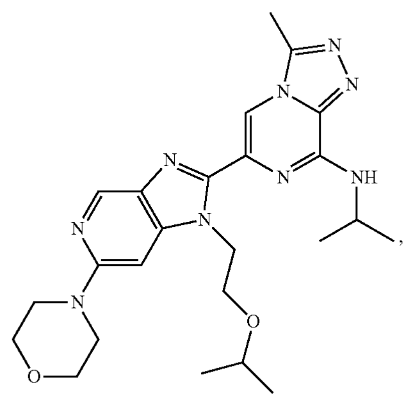 [SMILES: Cc1nnc2c(NC(C)C)nc(-c3nc4cnc(N5CCOCC5)cc4n3CCOC(C)C)cn12] |
| I-5 | 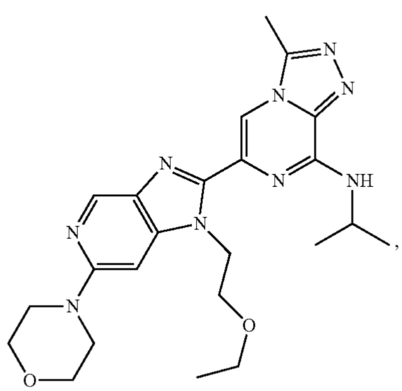 [SMILES: CCOCCn1c(-c2cn3c(C)nnc3c(NC(C)C)n2)nc2cnc(N3CCOCC3)cc21] | I-6 | 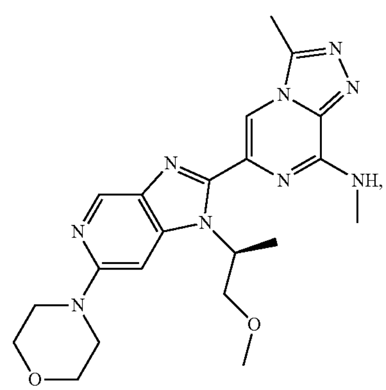 [SMILES: CNc1nc(-c2nc3cnc(N4CCOCC4)cc3n2[C@@H](C)COC)cn2c(C)nnc12] |
| I-7 | 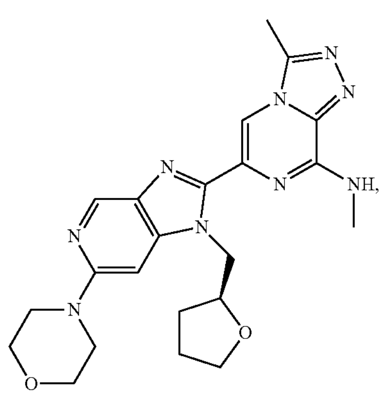 [SMILES: CNc1nc(-c2nc3cnc(N4CCOCC4)cc3n2C[C@@H]2CCCO2)cn2c(C)nnc12] | I-8 | 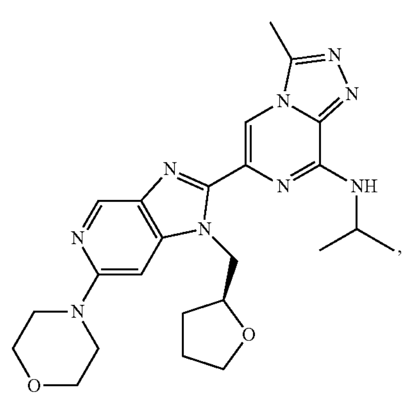 [SMILES: Cc1nnc2c(NC(C)C)nc(-c3nc4cnc(N5CCOCC5)cc4n3C[C@@H]3CCCO3)cn12] |

-continued

| # | Structure | # | Structure |
|---|---|---|---|
| I-9 | 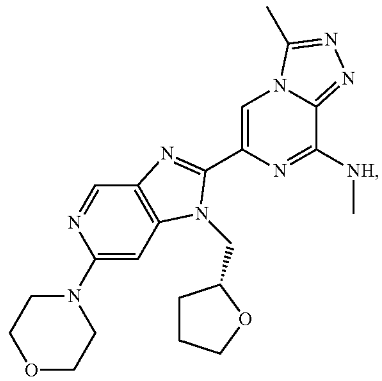 [SMILES: CNc1nc(-c2nc3cnc(N4CCOCC4)cc3n2C[C@H]2CCCO2)cn2c(C)nnc12] | I-10 | 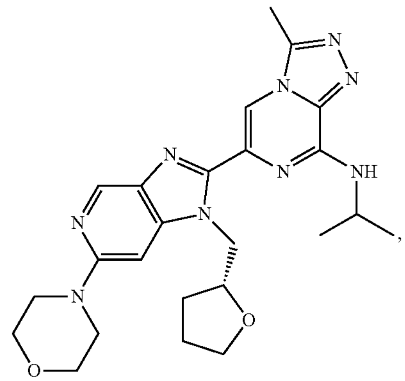 [SMILES: Cc1nnc2c(NC(C)C)nc(-c3nc4cnc(N5CCOCC5)cc4n3C[C@H]3CCCO3)cn12] |
| I-11 | 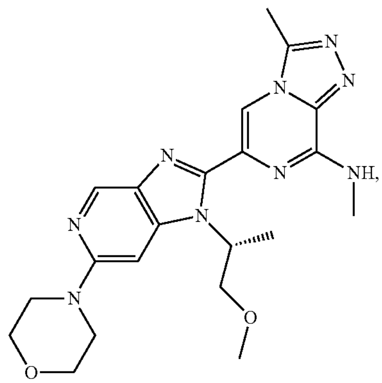 [SMILES: CNc1nc(-c2nc3cnc(N4CCOCC4)cc3n2[C@H](C)COC)cn2c(C)nnc12] | I-12 | 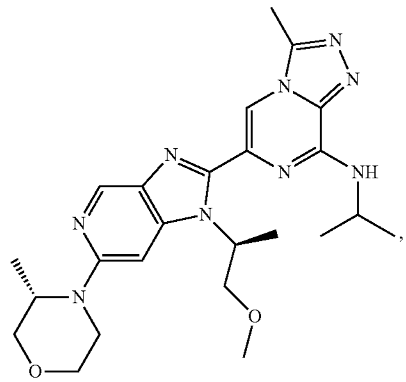 [SMILES: COC[C@H](C)n1c(-c2cn3c(C)nnc3c(NC(C)C)n2)nc2cnc(N3CCOC[C@@H]3C)cc21] |
| I-13 | 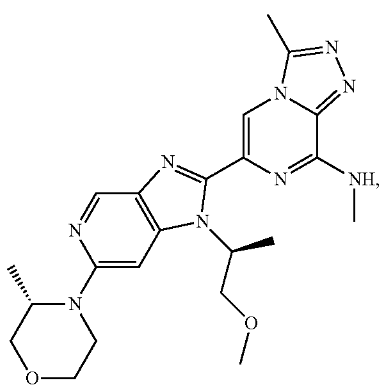 [SMILES: CNc1nc(-c2nc3cnc(N4CCOC[C@@H]4C)cc3n2[C@@H](C)COC)cn2c(C)nnc12] | I-14 | 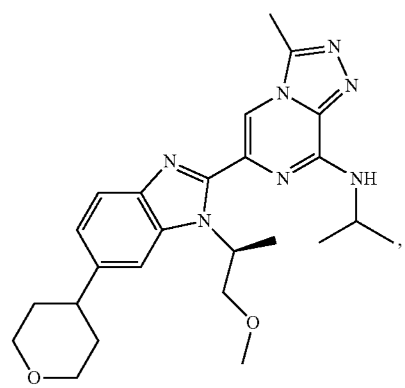 |
| I-15 | 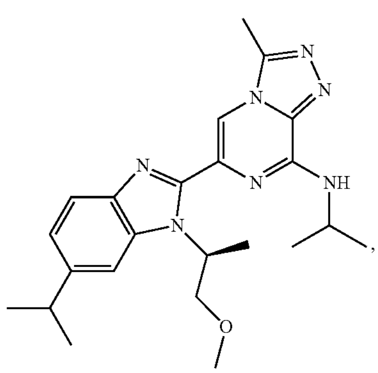 [SMILES: COC[C@H](C)n1c(-c2cn3c(C)nnc3c(NC(C)C)n2)nc2ccc(C(C)C)cc21] | I-16 | 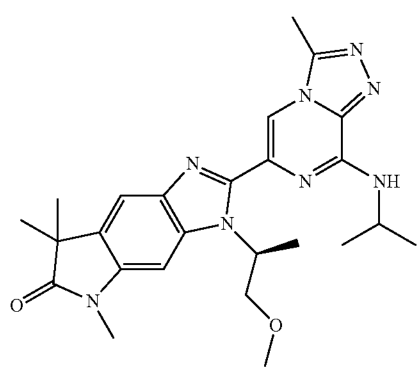 |

| # | Structure | # | Structure |
|---|---|---|---|
| I-17 | 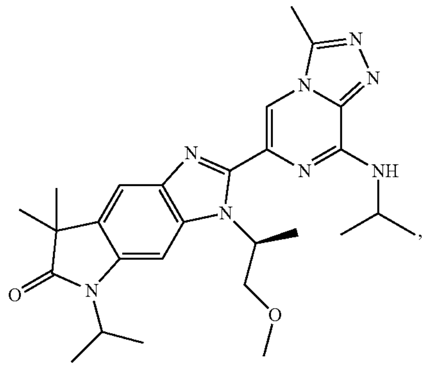 [SMILES: COC[C@H](C)n1c(-c2cn3c(C)nnc3c(NC(C)C)n2)nc2cc3c(cc21)N(C(C)C)C(=O)C3(C)C] | I-18 | 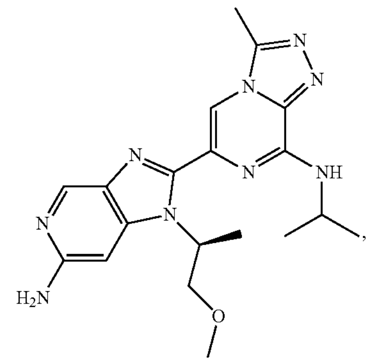 |
| I-19 | 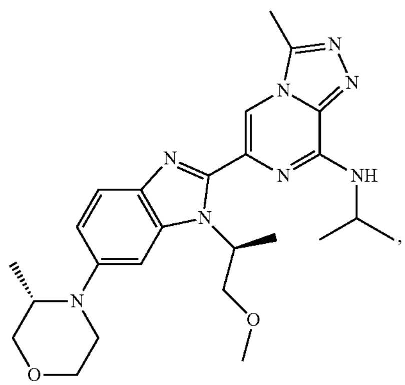 [SMILES: COC[C@H](C)n1c(-c2cn3c(C)nnc3c(NC(C)C)n2)nc2ccc(N3CCOC[C@@H]3C)cc21] | I-20 | 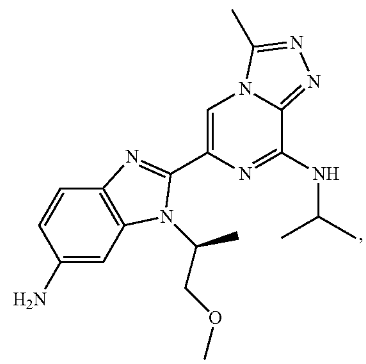 [SMILES: COC[C@H](C)n1c(-c2cn3c(C)nnc3c(NC(C)C)n2)nc2ccc(N)cc21] |
| I-21 | 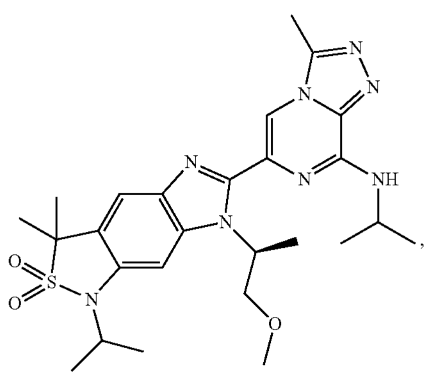 [SMILES: COC[C@H](C)n1c(-c2cn3c(C)nnc3c(NC(C)C)n2)nc2cc3c(cc21)N(C(C)C)S(=O)(=O)C3(C)C] | I-22 | 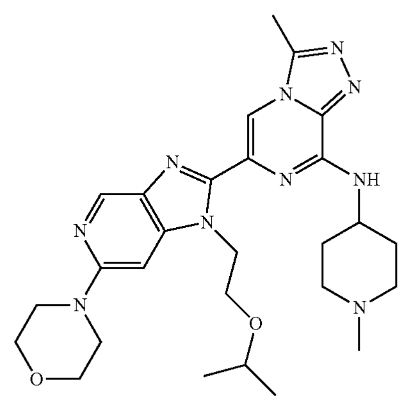 |
| I-23 | 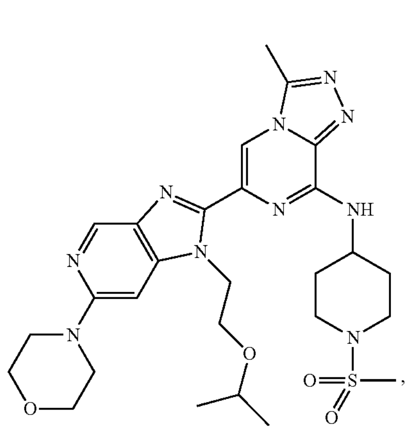 [SMILES: Cc1nnc2c(NC3CCN(S(C)(=O)=O)CC3)nc(-c3nc4cnc(N5CCOCC5)cc4n3CCOC(C)C)cn12] | I-24 | 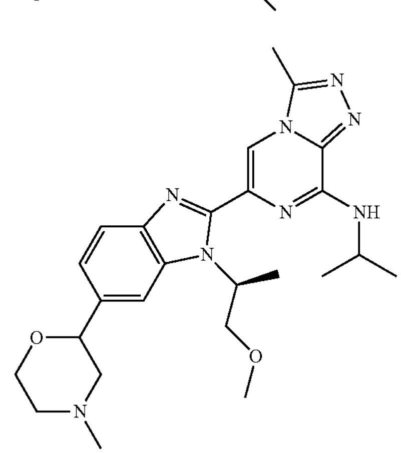 |

| # | Structure | # | Structure |
|---|---|---|---|
| I-25 | | I-26 | |
| I-27 | | I-28 | |
| | And | I-29 | | or a salt thereof.

15. A pharmaceutically acceptable salt of a compound according to claim 1.

16. A pharmaceutical composition comprising a compound according to claim 1, or a pharmaceutically acceptable salt thereof, and a carrier or diluent.

* * * * *